(12) United States Patent
Lundgren Åkerlund et al.

(10) Patent No.: US 11,725,188 B2
(45) Date of Patent: Aug. 15, 2023

(54) QUALITY ASSURANCE OF CHONDROCYTES

(71) Applicant: Xintela AB, Lund (SE)

(72) Inventors: Evy Lundgren Åkerlund, Bjarred (SE); Katarzyna Chmielarska Masoumi, Lund (SE)

(73) Assignee: Xintela AB, Lund (SE)

( * ) Notice: Subject to any disclaimer, the term of this patent is extended or adjusted under 35 U.S.C. 154(b) by 337 days.

(21) Appl. No.: 16/994,193

(22) Filed: Aug. 14, 2020

(65) Prior Publication Data

US 2020/0377858 A1 Dec. 3, 2020

Related U.S. Application Data

(60) Division of application No. 16/387,172, filed on Apr. 17, 2019, now Pat. No. 10,781,424, which is a
(Continued)

(30) Foreign Application Priority Data

Jun. 29, 2017 (SE) .................................. 1750849-0

(51) Int. Cl.
*C12N 5/077* (2010.01)
*C12N 5/00* (2006.01)
(Continued)

(52) U.S. Cl.
CPC ......... *C12N 5/0655* (2013.01); *C12N 5/0018* (2013.01); *C12N 5/0068* (2013.01); *C12Q 1/6851* (2013.01); *G01N 33/6887* (2013.01); *C12N 2500/38* (2013.01); *C12N 2501/58* (2013.01); *C12N 2501/585* (2013.01); *C12N 2513/00* (2013.01); *G01N 2333/70546* (2013.01)

(58) Field of Classification Search
None
See application file for complete search history.

(56) References Cited

U.S. PATENT DOCUMENTS

2009/0232777 A1 9/2009 Lundgren-Akerlund et al.

FOREIGN PATENT DOCUMENTS

EP 1613659 B1 1/2006
WO 9951639 A1 10/1999

OTHER PUBLICATIONS

Galois, Laurent; et al; "Bovine chondrocyte behaviour in three-dimensional type I collagen gel in terms of gel contraction, proliferation and gene expression" Biomaterials, 27, 79-90, 2006 (Year: 2006).*

(Continued)

*Primary Examiner* — David W Berke-Schlessel
(74) *Attorney, Agent, or Firm* — McNeill Baur PLLC

(57) ABSTRACT

The present invention relates to methods that are based on expression of integrin alpha10 and integrin alpha11 on chondrocytes, used for determining purity, quality, degree of chondrocytic identity, chondrocytic potency, and/or degree of chondrocytic phenotype of a composition comprising chondrocytes, as well as for isolating and enriching a population of high quality chondrocytes and controlling culturing and expanding of high quality chondrocytes. The present invention relates also to composition comprising chondrocytes.

15 Claims, 13 Drawing Sheets

Related U.S. Application Data continuation of application No. PCT/EP2018/067580, filed on Jun. 29, 2018.

(51) Int. Cl.
  *C12Q 1/6851* (2018.01)
  *G01N 33/68* (2006.01)

(56) References Cited

OTHER PUBLICATIONS

Zeitz, Cedric; Gullberg, Donald; "The integrin-collagen connection—a glue for tissue repair?" Journal of Cell Science, 129, 653-664, 2016 (Year: 2016).*

Hakala, Biran E; et al; "Human Cartilage gp-39,a Major Secretory Product of Articular Chondrocytes and Synovial Cells, Is a Mammalian Member of a Chitinase Protein Family" The Journal of Biochemistry, 268, 25803-25810, 1993 (Year: 1993).*

Bernstein et al., "Expression pattern differences between osteoarthritic chondrocytes and mesenchymal stem cells during chondrogenic differentiation", Osteoarhritis and Cartilage, vol. 18, pp. 1596-1607 (2010).

Camper et al., "Isolation, cloning and sequence analysis of the integrin subunit alpha10, a beta 1-associated collagen binding integrin expressed on chondrocytes", J. Biol. Chem., 273(32), pp. 20383-20389 (Aug. 7, 1998).

Camper et al., "Distribution of the collagen-binding integrin alpha 10 beta 1 during mouse development", Cell Tissue Res., 306, pp. 107-116 (2001).

Cortial et al., "Activation by IL-1 of bovine articular chondrocytes in culture within a 3D collagen-based scaffold. An in vitro model to address the effect of compounds with therapeutic potential in osteoarthritis," OsteoArthritis and Cartilage (2006) 14, 631-640.

Dai et al., "Detection and initial characterization of synovial lining fragments in synovial fluid", Rheumatology, vol. 45, pp. 533-537 (2006).

Dominici et al., "Minimal criteria for defining multipotent mesenchymal stromal cells. The International Society for Cellular Therapy position statement", Cytotherapy, 8(4), pp. 315-317 (2006).

Gigout et al., "Chondrocyte Aggregation in Suspension Culture is GFOGER-GPP- and β1 Integrin-dependent," The Journal of Biological Chemistry, vol. 283, No. 46, pp. 31522-31530, Nov. 14, 2008.

Gigout et al., "Chondrocytes Cultured in Stirred Suspension with Serum-Free Medium Containing Pluronic-68 Aggregate and Proliferate While Maintaining Their Differentiated Phenotype," Tissue Engineering: Part A, vol. 15, No. 00, 2009 (12 pages).

Goessler et al., "In vitro analysis of integrin expression during chondrogenic differentiation of mesenchymal stem cells and chondrocytes upon dedifferentiation in cell culture", Intl J. Mol. Med., 17(2), pp. 301-307 (2006).

Gouttenoire et al., "BMP-2 and TGF-Beta1 differntially control expression of type II procollagen and alpha10 and aplha11 integrins in mouse chondrocytes", European Journal of Cell Biology, 89(4), pp. 307-314 (Apr. 1, 2010).

Grassel et al., "Gene and protein expression profile of naive and osteo-chondrogenicaHy differentiated rat bone marrow-derived mesenchymal progenitor cells," International Journal of Molecular Medicine, vol. 23, Issue 6, pp. 745-755, Jun. 1, 2009.

Han et al., "Mesenchymal Stem Cells for Regenerative Medicine", Cells (www.mdpi,com/journal/cells) 8, 886 (2019) (32 pages).

International Search Report and Written Opinion of PCT/EP2018/067580, dated Aug. 31, 2018 (22 pages).

Kaps et al., "Human platelet supernatant promotes proliferation but not differentiation of articular chondrocytes", Med. Biol. Eng. Comput., 40(4), pp. 485-490 (Jul. 1, 2002).

Karlsen et al., "Human Primary Articular Chondrocytes, Chondroblasts-Like Cells, and Dedifferentiated Chondrocytes: Differences in Gene, MicroRNA, and Protein Expression and Phenotype," Tissue Engineering: Part C, vol. 17, No. 2, pp. 219-222, 2011.

Lehnert et al., "Cloning, sequence analysis, and chromosomal localization of the novel human intergrin alpha11 subunit", Genomics, 60(2), pp. 179-187 (1999).

Mennan et al., "Human Articular Chondrocytes Retain Their Phenotype in Sustained Hypoxia While Normoxia Promotes Their Immunomodulatory Potential", Cartilate 10(4), pp. 467-479 (2019).

Mobasheri et al., "Chondrocyte and mesenchymal stem cell-based therapies for cartilage repair in osteoarthritis and related orthopaedic conditions", Maturitas, 78, pp. 188-198 (2014).

Rapko et al., "Identification of the chondrocyte lineage using microfibril-associated glycoprotein-2, a novel marker that distinguishes chondrocytes from synovial cells", Tissue Engineering, 16(6), pp. 1367-1375 (Dec. 1, 2020).

Stebulis et al., "Fibroblast-like Synovial Cells Derived From Synovial Fluid", J. Rheumatol., 32(2), pp. 301-306 (2005).

Third Party Observation submitted in International Application No. PCT/EP2018/067580 on Jun. 28, 2019 by Anonymous (4 pages).

Varas et al., "Alpha10 integrin expression is up-regulated on fibroblast growth factor-2-treated mesenchymal stem cells with improved chondrogenic differentiation potential", Stem Cells and Devl., 16, pp. 965-978 (2007).

Bengtsson, Therese et al., "Loss of α10β1 integrin expression leads to moderate dyfunction of growth plate chondrocytes", Journal of Cell Science 118, 2005, 929-936.

Vogel, Christine et al., "Insights into the regulation of protein abundance from proteomic and transcriptomic analyses", Nature Reviews, Genetics, vol. 13, Apr. 2012.

* cited by examiner

Collagen II    Collagen I    Integrin α10

QUALITY ASSURANCE OF CHONDROCYTES

CROSS REFERENCE TO RELATED APPLICATIONS

This application is a divisional of U.S. application Ser. No. 16/387,172, filed on Apr. 17, 2019, which is a non-provisional continuation application filed under 35 U.S.C. § 111(a) of International Application No. PCT/EP2018/067580, filed on Jun. 29, 2018, which claims priority to Swedish Application No. SE 1750849-0, filed on Jun. 29, 2017, all of which are incorporated by reference in their entirety.

TECHNICAL FIELD

The present invention relates to chondrocyte compositions having high quality as well as methods for quality assurance and quality control of chondrocyte compositions.

BACKGROUND

Damage to the hyaline cartilage of a joint has a limited intrinsic capacity to heal after an injury. This can lead to accelerated degeneration of the joint and early-onset osteoarthritis. Today, there is growing demand for preservation of native articular cartilage to delay joint arthroplasties.

The human adult articular chondrocyte is a unique cell type that has reached a fully differentiated state as an end point of development. Within the cartilage matrix, chondrocytes regulate the homeostasis of the cartilage and maintain the matrix constituents in a low-turnover state of equilibrium.

Chondrocytes, the only type of cells in cartilage, express a number of different integrins. The integrins are a large family of transmembrane glycoproteins that mediate cell-cell and cell-matrix interactions. All known members of this superfamily are non-covalently associated heterodimers composed of an alpha- and a beta-subunit. The integrin alpha10beta1 is a major collagen-binding integrin on chondrocyte. It is expressed by differentiated chondrocytes as well as by MSCs with chondrogenic differentiation potential. Integrin alpha11beta1, on the other hand, is expressed by fibroblastic cells, including synovial fibroblasts. Integrin alpha11beta1 is also expressed by chondrocytes in monolayer cultures that may have partially dedifferentiated and produce the fibrous collagen type I instead of the cartilage collagen type II and thus provide a way to determine the purity and quality of chondrocyte preparations.

Chondrocyte based cell therapy for the treatment of articular cartilage injury is a promising method aiming to repair and restore the hyaline cartilage.

A major limitation of chondrocyte based cell therapies is related to the procedure where the cartilage matrix is removed enzymatically from the cartilage biopsy to isolate the chondrocytes. During this procedure cells from non-cartilage tissues such as the synovium, may contaminate the chondrocyte preparations (Dai et al. 2006, Stebuils et al. 2005), thereby having an impact on the purity and the quality of the chondrocyte preparations used for implantation. In addition, chondrocytes often dedifferentiate once isolated from the cartilage matrix (Rapko et al. 2009). This leads to a loss of their specialized chondrocyte characteristics which can be detected as a switch in synthesis of collagen type II to collagen type I. Hence, there is a need for a robust procedure for quality control of chondrocyte quality.

SUMMARY

The present inventors have found a correlation between the expression levels of the cell surface proteins integrin alpha10beta1 and integrin alpha11beta1 and the quality of isolated and cultured chondrocytes and thus a new way to define and quality assure and/or quality control chondrocyte preparations.

The present disclosure is based on the finding that an integrin alpha10 to integrin alpha11 expression ratio of at least 4 to 1 is indicative of high quality chondrocyte composition and/or product. Although integrin alpha10 and integrin alpha11 expression levels vary depending on the culturing conditions, their ratio is predictive of a high quality chondrocyte composition.

Moreover, the present inventors have also found that:
- expression of integrin alpha10 may be indicative of chondrocyte identity;
- expression of integrin alpha10 together with integrin alpha11 may be indicative of partially dedifferentiated chondrocytes;
- expression of integrin alpha10 and low or substantially no expression of integrin alpha11 may be indicative of differentiated chondrocytes, and
- expression of integrin alpha11 and low or substantially no expression of integrin alpha10 may be indicative of non-chondrocyte identity, including highly dedifferentiated chondrocytes, fibroblast-like cells and/or other contaminant cells.

Thus, in one aspect, the present disclosure relates to a composition comprising chondrocytes, wherein said composition have an integrin alpha10 to integrin alpha11 expression ratio of at least 4 to 1.

In another aspect, the present disclosure relates to a method for determining quality of a composition comprising chondrocytes, wherein the quality determination comprises one or more of the following criteria:
- identity of the chondrocytes,
- differentiation state of the chondrocytes,
- purity of the chondrocytes, and
- potency of the chondrocytes the method comprising the steps of:
a) providing a candidate composition comprising chondrocytes;
b) analyzing the expression levels of integrin alpha10 and integrin alpha11 in said composition;
c) comparing the expression level of integrin alpha10 to the expression level of integrin alpha11, wherein an integrin alpha10 to integrin alpha11 expression ratio of at least 4 to 1 is indicative of
- chondrocytic identity of the chondrocytes in the chondrocyte composition,
- differentiated state of the chondrocytes in the chondrocyte composition,
- purity of the chondrocyte composition, and/or
- potency of the chondrocytes of the chondrocyte composition, and thereby is indicative of a high quality chondrocyte composition.

Hence, the present disclosure relates to methods for quality assuring and quality control chondrocytes compositions.

In a further aspect, the present disclosure relates to a method for isolating a population of high quality chondrocytes, the method comprising the steps of:
 a) providing a candidate composition comprising chondrocytes;
 b) analyzing expression of integrin alpha10 and integrin alpha11 in said composition; and
 c) enriching chondrocytes having an integrin alpha10 to integrin alpha11 expression ratio of at least 4 to 1, thus obtaining an isolated population of high quality chondrocytes.

In a further aspect, the present disclosure relates to a method for manufacturing a population of high quality chondrocytes, the method comprising the steps of:
 a) providing a candidate composition comprising chondrocytes;
 b) analyzing expression of integrin alpha10 and integrin alpha11 in said composition; and
 c) expanding chondrocytes having an integrin alpha10 to integrin alpha11 expression ratio of at least 4 to 1, thus manufacturing a population of high quality chondrocytes.

In one aspect, the present disclosure concerns a method for optimizing chondrocytic potency of a composition comprising chondrocytes, the method comprising inducing expression of integrin alpha10.

In one aspect, the present disclosure concerns a method of increasing proliferation rate of chondrocytes, the method comprising inducing expression of integrin alpha10.

In one aspect, the present disclosure concerns an in vitro cell preparation or cell culture of chondrocytes having an integrin alpha10 to integrin alpha11 expression ratio of at least 4 to 1.

In one aspect, the current invention concerns use any one of the methods described herein, for
 a) quality assuring chondrocyte compositions;
 b) monitoring of consistency and/or reproducibility of chondrocyte compositions;
 c) predicting potency of chondrocyte compositions and cultures;
 d) in-process control chondrocyte compositions
 e) in-process control of expansion of chondrocyte compositions;
 f) conducting a potency assay of a chondrocyte composition;
 g) conducting release test of chondrocyte compositions; and/or
 h) prediction of clinical outcome and/or of chondrocyte compositions.

DETAILED DESCRIPTION

Definitions

Figure 1A:
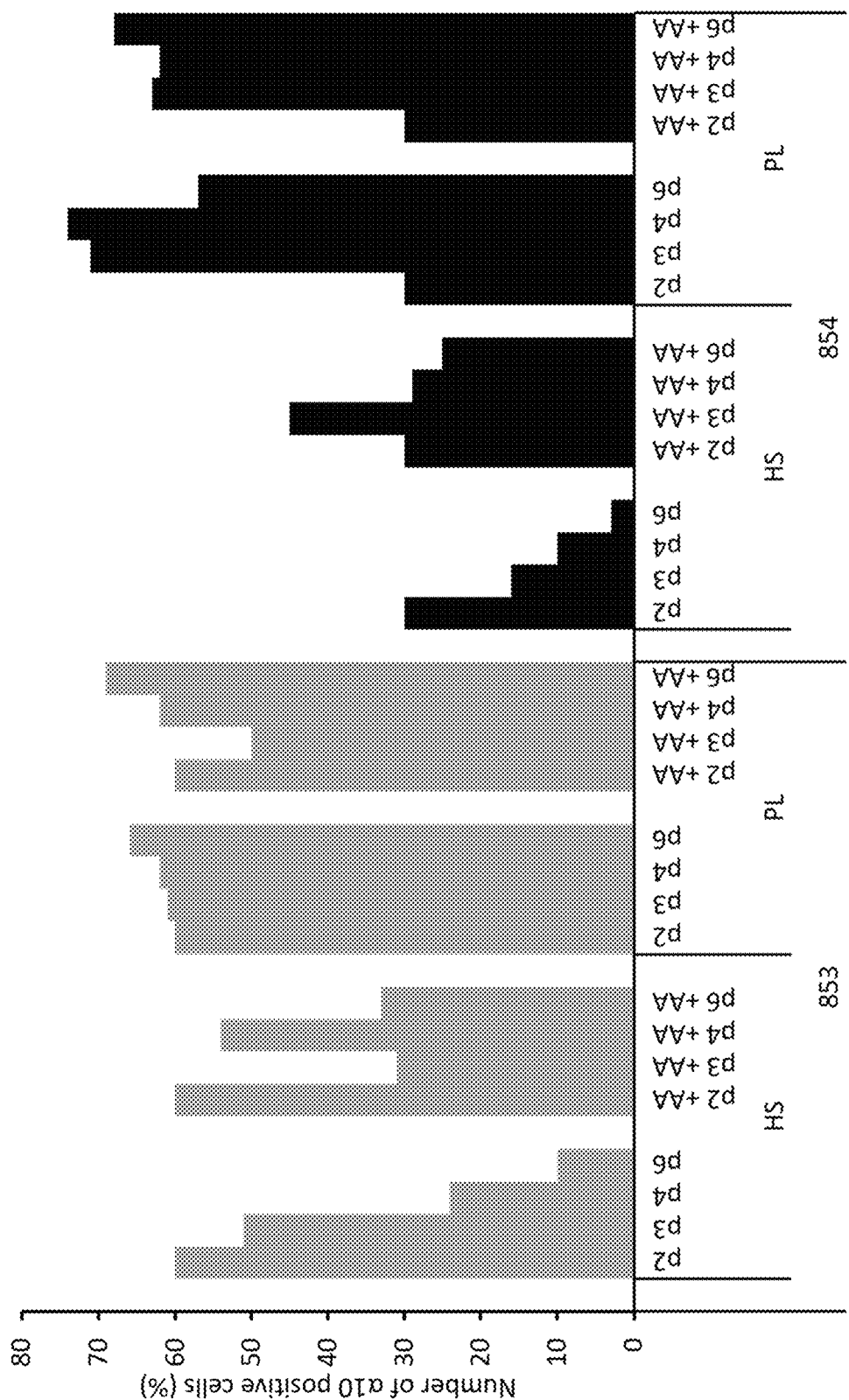
FIG. 1A. Flow cytometry analysis of alpha10beta1-expression on two human chondrocyte preparation, 853 and 854, cultured in monolayer for 2-6 passages. The chondrocytes were cultured in media containing either human serum (HS) or platelet lysate (PL) with or without addition of ascorbic acid (A). The integrin expression decreases when chondrocytes are cultured in HS only.

"Integrin alpha10" as used herein refers to the alpha10 subunit of the heterodimeric protein integrin alpha10beta1 as well as to the heterodimeric protein integrin alpha10beta1. This denotation does not exclude the presence of the beta1 subunit bound to the alpha10 subunit thus forming an integrin alpha10beta1 heterodimer. The human integrin alpha10 chain sequence is known and publicly available at GenBank™/EBI Data Bank accession number AF074015.

"Anti-integrin alpha10 antibody" as used herein refers to an antibody capable of recognizing and binding at least to the integrin alpha10 subunit but also to the heterodimeric protein integrin alpha10beta1. These antibodies may be antibodies that recognize an epitope of the heterodimeric protein integrin alpha10beta1, wherein the epitope comprises amino acid residues of both the alpha10 and the beta1 subunits. These antibodies may also be antibodies that recognize an epitope of the heterodimeric protein integrin alpha10beta1, wherein the epitope comprises amino acid residues of only the alpha10 subunit.

"Integrin alpha11" as used herein refers to the alpha11 subunit of the heterodimeric protein integrin alpha11beta1 as well as the heterodimeric protein integrin alpha11beta1. This denotation does not exclude the presence of the beta1 subunit bound to the alpha11 subunit thus forming an integrin alpha10beta1 heterodimer.

"Anti-integrin alpha11 antibody" as used herein refers to an antibody capable of recognizing and binding to at least the integrin alpha11 subunit but also to the integrin alpha11 subunit of the heterodimeric protein integrin alpha11 beta1. These antibodies may be antibodies that recognize an epitope of the heterodimeric protein integrin alpha11 beta1, wherein the epitope comprises amino acid residues of both the alpha11 and the beta1 subunits. These antibodies may also be antibodies that recognize an epitope of the heterodimeric protein integrin alpha11beta1, wherein the epitope comprises amino acid residues of only the alpha11 subunit.

The term "integrin alpha10/11" refers to either integrin alpha10 or integrin alpha11, or to both integrin alpha10 and integrin alpha11.

"Ascorbic acid" as used herein includes (R)-3,4-dihydroxy-5-((S)-1, 2-dihydroxyethyl)furan-2(5H)-one derivatives thereof, such as L-Ascorbic acid 2-phosphate-sesquimagnesium salt hydrate.

The term "identifying" as used herein refers to the action of recognizing a cell as being a certain type of cell, e.g. a chondrocyte or a fibroblast-like cell. An alternative term to identifying is "detecting", which is used herein with the same meaning.

The terms "isolating", "sorting" "selecting", and "depleting" as used herein refer to the action of identifying a cell as being a certain type of cell and separating it from cells that do not belong to the same cell type or to a differentiation state.

The term "composition" as used herein may refer to a preparation of cells, such as a preparation of chondrocytes. The term "composition" as used herein may also refer to a culture of cells, such as a culture of chondrocytes. A composition of chondrocytes may also be a chondrocyte product. Examples of chondrocyte products are known to the person of skilled in the art and may be isolated chondrocytes in suspension, chondrocytes cultured in monolayer, and three-dimensional (3D) cultures such as spheroids, pellets, cell sheets and chondrocytes cultured in scaffolds. For example chondrocytes scaffolds may be made using 3D hydrogels, collagen matrices, hyaluronan, poly-glycolic acid (PGA)-Fibrin and poly-lactic acid (PLA).

The term "potency" or "cell potency" as used herein may be defined as a quantitative measure of relevant biologic function. A potency assay provide a mechanism by which a manufacturing process and the final cell product for batch release are scrutinized for quality, consistency and stability. Analysis of the Expression of Integrin Subunits Alpha10 and Alpha11

A key step in the methods of the present invention is the detection of integrin alpha10 expression and integrin alpha11 expression.

In one embodiment, analysis of the expression is conducted by a method selected from the group consisting of flow cytometry, ELISA, Western Blot, immunoprecipitation, dot blot, qPCR, immunoassay, immunofluorescence, immunohistochemistry, gene expression analysis and any other suitable method. Preferably, the analysis of the expression of integrin alpha10 and/or alpha11 is conducted by flow cytometry using specific antibodies. Multi-color analyses may be employed with the flow cytometry, which is particularly convenient. The person of skill in the art is adequately qualified to determine the method of choice for determining degree of expression, for each individual case.

The expressions of integrin alpha10 and/or integrin alpha11 can be analyzed using the same kind of methods. In one embodiment, the integrin alpha10/11 expression is analyzed by measuring the corresponding protein expression.

In another embodiment, the expression of integrin alpha10/11 is analyzed by measuring integrin alpha10/11 mRNA expression. Detection of mRNA expression of a specific protein is well known to the skilled man in the art, and is generally done by probing the mRNA with a DNA or RNA probe specific for the mRNA of interest, under hybridization conditions where the probe is not hybridizing to other mRNA molecules. Different polymerase chain reactions (PCR) may also be used, which is obvious to the skilled man in the art.

In one embodiment, the analysis comprises quantitative determination of the expression of integrin alpha10 and integrin alpha11.

Several methods are known to the person skilled in the art for detection of expression of cellular markers. Accordingly, in one embodiments of the present disclosure the detection of expression of integrin alpha10/11 by a cell is determined by a method selected from the group consisting of immunoassay, flow cytometry, immunofluorescence, immunoprecipitation, immunohistochemistry and western blot. In still a further embodiment, the expression of integrin alpha10/11 is detected by any immunoassay, such as the methods described in Immunochemical protocols (Methods in molecular biology, Humana Press Inc). The detection may be performed by various methods, e.g. any immune method known to the skilled man in the art, such as immunoprecipitation, Western blotting, magnetic-activated cell sorting (MACS) or flow cytometry methods, e.g. fluorescence activated cell sorting (FACS).

In some embodiments, the integrin alpha10/11 protein expression is detected by an anti-integrin alpha10/11 antibody, wherein said antibody may be a monoclonal antibody, a polyclonal antibody, a single chain antibody or fragment thereof. In another embodiment, the antibody is a non-human antibody, a chimeric antibody, a bispecific antibody, a humanized antibody or a human antibody.

Said antibody may be covalently bound to a detectable moiety, such as a detectable moiety selected from the group consisting of a fluorophore, an enzyme or a radioactive tracer or radioisotope. In a preferred embodiment, the antibody is labeled with one or more fluorophore(s). Said fluorophore may be selected from the group consisting of phycoerythrin, allophycocyanin, fluorescein, Texas red, Alexa Fluor 647, and brilliant dyes. Many other fluorophores may be used and the skilled person will choose the most suitable one according to the specific detection method and also according to the characteristics of the antibody used. In some embodiments, fluorophores with non-overlapping emission spectra are bound to the anti-integrin alpha10 antibody and the anti-integrin alpha11 antibody.

In one embodiment, said antibody is attached to a solid support, for example to magnetic beads.

In one embodiment, said antibody is attached to biotin.

Furthermore, said antibody may have an isotype selected from the group consisting of IgA, IgD, IgG and IgM.

In one embodiment, the antibody is:
a) a monoclonal antibody, produced by the hybridoma cell line deposited at the Deutsche Sammlung von Mikroorganismen und Zellkulturen GmbH under the accession number DSM ACC2583; or
b) an antibody which competes for binding to the same epitope as the epitope bound by the monoclonal antibody produced by the hybridoma deposited at the Deutsche Sammlung von Mikroorganismen und Zellkulturen GmbH under the accession number DSM ACC2583; or
c) a fragment of a) or b), wherein said fragment is capable of binding specifically to the extracellular I-domain of the integrin alpha10 chain.

Identification may as well be performed by any specific molecule, such as a protein or peptide, binding specifically to the integrin alpha10/11 molecule. Examples of such proteins or peptides are natural ligands, binding to the integrin alpha10/11 molecule. Such natural ligands may be made recombinant, chemically synthesized, or purified from a natural source.

Chondrocyte Composition

The inventors have found that a chondrocyte composition characterized by an integrin alpha10 to integrin alpha11 expression ratio of at least 4 to 1 is a high quality chondrocyte composition.

Hence, one aspect of the present disclosure relates to a composition comprising chondrocytes, wherein said composition have an integrin alpha10 to integrin alpha11 expression ratio of at least 4 to 1.

In one embodiment, the integrin alpha10 to integrin alpha11 expression ratio is at least 4 to 1, such as at least 5 to 1, such as at least 10 to 1, such as at least 15 to 1, such as at least 20 to 1, such as at least 25 to 1, such as at least 30 to 1, such as at least 35 to 1, such as at least 40 to 1, such as at least 45 to 1, such as at least 50 to 1, such as at least 60 to 1, such as at least 70 to 1, such as at least 80 to 1, such as at least 90 to 1, such as at least 100 to 1, such as at least 150 to 1, such as at least 200 to 1. In another embodiment, said integrin alpha10 to integrin alpha11 expression ratio is below 200 to 1, such below 150 to 1, such as below 100 to 1, such as below 50 to 1, such as below 25 to 1.

In one embodiment, the integrin alpha11 expression is at the most 25% of the integrin alpha10 expression, such as at the most 20% of the integrin alpha10 expression, such as at the most 15% of the integrin alpha10 expression, such as at the most 10% of the integrin alpha10 expression, such as at the most 5% of the integrin alpha10 expression, such as at the most 4% of the integrin alpha10 expression, such as at the most 3% of the integrin alpha10 expression, such as at the most 2% of the integrin alpha10 expression, such as at the most 1% of the integrin alpha10 expression, such as at the most 0.5% of the integrin alpha10 expression.

In yet another embodiment, substantially no integrin alpha11 is expressed.

In one embodiment, the composition may comprise differentiated chondrocytes, and said differentiated chondrocytes may express integrin alpha10 and substantially no integrin alpha11.

"Substantially no integrin alpha11 expression" as used herein means that the percentage of cells expressing integrin alpha11, but not expressing integrin alpha10, that is single alpha11 cells, is below 20%. In some embodiments, the percentage of cells expressing integrin alpha11, but not expressing integrin alpha10 is below 15%, such as below 10%, such as below 5%, such as below 4%, such as below 3%, such as below 2%, such as below 1%, such as below 0.5%.

In one embodiment, the composition may comprise partially dedifferentiated chondrocytes, and said partially dedifferentiated chondrocytes may express both integrin alpha10 and integrin alpha11. Partially dedifferentiated chondrocytes are chondrocytes that have reverted to a more fibroblast-like cell. They may be able to redifferentiate into chondrocytes depending on the cultivation conditions.

In one embodiment, the composition comprising chondrocytes is selected from the group consisting of a cartilage tissue preparation, a tissue preparation comprising chondrocytes, a monolayer chondrocyte cell culture, and a three-dimensional (3D) chondrocyte cell culture, such as spheroids, pellets or cell sheets.

In one embodiment, the composition comprising chondrocytes is derived from a cartilage tissue, a chondrocyte comprising tissue, a monolayer chondrocyte cell culture, and a three-dimensional chondrocyte cell culture, such as spheroids, pellets, cell sheets or from chondrocytes cultured in a scaffold.

In one embodiment, the composition comprising chondrocytes may comprise mammalian cells.

In one embodiment, the composition comprising chondrocytes may comprise human cells.

In one embodiment, the composition comprising chondrocytes may comprise equine cells.

In one embodiment, the composition comprising chondrocytes may comprise canine cells.

In one embodiment, integrin alpha10 and/or integrin alpha11 is expressed on the cell surface of a mammalian chondrocyte or a fibroblast-like cell.

In one embodiment, the integrin alpha10 and/or integrin alpha11 is expressed as a heterodimer in combination with an integrin beta1.

In one embodiment, the composition comprising chondrocytes may be substantially free from contaminating cells, wherein the contaminating cells may express integrin alpha11 but not integrin alpha10, that is they may be single alpha11 cells. Cells expressing integrin alpha11 but not integrin alpha10 may be contaminating cells, fibroblast-like cells or highly dedifferentiated cells. Cells express integrin alpha11 but not integrin alpha10 may be non-functional chondrocytes and hence they may be a minor component of the chondrocyte composition.

The lower is the number of cells expressing integrin alpha11 but not integrin alpha10, the higher is the number of chondrocytes in the composition, hence the higher is the degree of purity of the chondrocyte composition.

It may be possible to optimize the culture conditions of dedifferentiated chondrocytes so to induce expression of integrin alpha10 and thus redifferentiate the chondrocytes. Hence, a composition comprising chondrocytes may be defined as being substantially free from contaminating cells, when the percentage of cells expressing integrin alpha11, but not expressing integrin alpha10, is below 20%. In some embodiments, the percentage of cells expressing integrin alpha11, but not expressing integrin alpha10 may be below 15%, such as below 10%, such as below 5%, such as below 4%, such as below 3%, such as below 2%, such as below 1%, such as below 0.5%.

In one embodiment, the composition comprising chondrocytes may comprise at least 70% chondrocytes, such as at least 75%, such as at least 80%, such as at least 85%, such as at least 90%, such as at least 95%, such as at least 98%, such as at least 99%, such as 100% chondrocytes, out of the total composition or population of cells.

In one embodiment, the composition comprising chondrocytes may comprise at least 80%, such as at least 85%, such as at least 90%, such as at least 95%, such as at least 98%, such as at least 99%, such as 100% chondrocytes, out of the total composition or population of cells.

In one embodiment, the composition comprising chondrocytes may further express a secondary marker selected from the group consisting of CEP-68/CRTAC1, GP-39 cartilage glycoprotein, CD44, CD166, Collagen IIA, Collagen IIB, Aggrecan, Alizarian Red (neg), Alcian Blue, CRTAC1, CEP-68, CD146, CD90, CD49e, CD63 and Sca-1.

The chondrocyte composition disclosed herein may be formulated as a cell suspension, a cell culture, a cell monolayer, or a three-dimensional (3D) scaffold, such as spheroids, pellets, cell sheets and chondrocytes cultured in scaffolds. Examples of 3D scaffolds are known in the art and may be based on the use of for example 3D hydrogels, collagen matrices, hyaluronan, poly-glycolic acid (PGA)-fibrin and poly-lactic acid (PLA).

The chondrocyte composition disclosed herein may be then used for several applications, for example in the area of cartilage regeneration and cartilage repair. The herein disclosed chondrocyte compositions may be suitable for both autologous and allogenic use.

Method for Determining Purity Quality, Degree of Chondrocytic Identity, Functional Potency, Differentiation State and/or Chondrocytic Phenotype In one aspect, the present disclosure relates to a method for determining quality of a composition comprising chondrocytes, wherein the quality determination comprises one or more of the following criteria:
identity of the chondrocytes,
differentiation state of the chondrocytes,
purity of the chondrocytes, and
potency of the chondrocytes,
the method comprising the steps of:
a) providing a candidate composition comprising chondrocytes;
b) analyzing the expression levels of integrin alpha10 and integrin alpha11 in said composition;
c) comparing the expression level of integrin alpha10 to the expression level of integrin alpha11,
wherein an integrin alpha10 to integrin alpha11 expression ratio of at least 4 to 1 is indicative of
chondrocytic identity of the chondrocytes in the chondrocyte composition,
differentiated state of the chondrocytes in the chondrocyte composition,
purity of the chondrocyte composition, and/or
potency of the chondrocytes of the chondrocyte composition,
and thereby is indicative of a high quality chondrocyte composition.

In one embodiment, said method may comprise comparing the expression level of integrin alpha10 to the expression level of integrin alpha11, wherein at the most 20%, such as at the most 15%, such as at the most 10%, such as at the most 5%, such as at the most 4%, such as at the most 3%, such as at the most 2%, such as at the most 1%, such as at the most 0.5%, of the cells in the chondrocyte composition expressing alpha11 and expressing no or substantially no integrin alpha10, that is single alpha11 cells, is indicative of purity of the chondrocyte composition.

In fact, the lower is the number of cells expressing integrin alpha11 but not integrin alpha10 (single alpha11 cells), the higher is the number of chondrocytes in the composition, hence the higher is the degree of purity of the chondrocyte composition.

In one embodiment, said method may comprise comparing the expression level of integrin alpha10 to the expression level of integrin alpha11, wherein expression of integrin alpha10 together with integrin alpha11 is indicative of a partially dedifferentiated chondrocyte composition. For example, a chondrocyte expressing both integrin alpha10 and integrin alpha11 may be a partially dedifferentiated chondrocyte.

In one embodiment, said method may comprise comparing the expression level of integrin alpha10 to the expression level of integrin alpha11, wherein expression of integrin alpha10 and substantially no expression of integrin alpha11 may be indicative of a differentiated chondrocyte composition. For example, a chondrocyte expressing integrin alpha10, but substantially not expressing integrin alpha11 may be a differentiated chondrocyte.

In one embodiment, said method may comprise quantitative determination of the expression of integrin alpha10 and integrin alpha11.

In one embodiment, said method may comprise comparing the expression level of integrin alpha10 to the expression level of integrin alpha11, wherein expression of integrin alpha10 and substantially no expression of integrin alpha11 may be indicative of a differentiated chondrocyte composition. "Substantially no expression of integrin alpha11" may refer to less than 20% of the cells comprised in the composition expressing integrin alpha11, but not expressing integrin alpha10. In some embodiments, the percentage of cells expressing integrin alpha11, but not expressing integrin alpha10, is below 15%, such as below 10%, such as below 5%, such as below 4%, such as below 3%, such as below 2%, such as below 1%, such as below 0.5%.

The inventors have also found that expression of integrin alpha11 and substantially no expression of integrin alpha10 in a chondrocyte may be indicative of fibroblastic-like cells.

In one embodiment, said method further comprises detecting expression of a secondary chondrocyte or fibroblast marker selected from the group consisting of CEP-68/CRTAC1, GP-39 cartilage glycoprotein, CD44, CD166, Collagen IIA, Collagen IIB, Aggrecan, Alizarian Red (neg), Alcian Blue, CRTAC1, CEP-68, CD146, CD90, CD49e, CD63 and Sca-1. The person of skill in the art is adequately qualified to determine the method of choice for detecting expression of said marker, for each individual case.

In one embodiment, the method is performed in vitro.

In one embodiment, the analysis of the expression of integrin alpha10 and integrin alpha11 is conducted after culturing the cells in a medium optimized for inducing expression of integrin alpha10. Induction of integrin alpha10 expression is described herein in the present disclosure.

In one embodiment, the analysis of the expression of integrin alpha10 and integrin alpha11 is conducted simultaneously. In another embodiment, the analysis of the expression of integrin alpha10 and integrin alpha11 is conducted separately. See for example the data reported in example 4 and FIGS. 7 and 9.

Method for Isolating a Population of High Quality Chondrocytes

In one aspect, the present invention concerns a method for isolating a population of high quality chondrocytes, the method comprising the steps of:
a) providing a candidate composition comprising chondrocytes;
b) analyzing expression of integrin alpha10 and integrin alpha11 in said composition; and
c) selecting chondrocytes having an integrin alpha10 to integrin alpha11 expression ratio of at least 4 to 1, thus obtaining a population of high quality chondrocytes.

In one embodiment, a population of high quality chondrocytes may be a a population of chondrocytes characterized by an integrin alpha10 to integrin alpha11 expression ratio of at least 4 to 1.

In one embodiment, said method may comprise quantitative determination of the expression of integrin alpha10 and integrin alpha11.

In one embodiment, the integrin alpha10 and/or the integrin alpha11 may be expressed on the cell surface of a mammalian chondrocyte and/or a fibroblast-like cell.

In one embodiment, said obtained isolated population of high quality chondrocytes may be an enriched and/or purified population of chondrocytes. Preferably, said obtained isolated population of chondrocytes may be enriched and/or purified in that the chondrocytes of said population have a high integrin alpha10 to integrin alpha11 expression ratio. In one embodiment, the integrin alpha10 to integrin alpha11 expression ratio in the obtained isolated population of chondrocytes is at least 4 to 1, such as at least 5 to 1, such as at least 10 to 1, such as at least 15 to 1, such as at least 20 to 1, such as at least 25 to 1, such as at least 30 to 1, such as at least 35 to 1, such as at least 40 to 1, such as at least 45 to 1, such as at least 50 to 1, such as at least 60 to 1, such as at least 70 to 1, such as at least 80 to 1, such as at least 90 to 1, such as at least 100 to 1, such as at least 150 to 1, such as at least 200 to 1.

In one embodiment, the integrin alpha11 expression is at the most 25% of the integrin alpha10 expression, such as at the most 20% of the integrin alpha10 expression, such as at the most 15% of the integrin alpha10 expression, such as at the most 10% of the integrin alpha10 expression, such as at the most 5% of the integrin alpha10 expression, such as at the most 4% of the integrin alpha10 expression, such as at the most 3% of the integrin alpha10 expression, such as at the most 2% of the integrin alpha10 expression, such as at the most 1% of the integrin alpha10 expression, such as at the most 0.5% of the integrin alpha10 expression.

In yet another embodiment, substantially no integrin alpha11 is expressed in the obtained isolated population of chondrocytes.

In one embodiment, the obtained composition may comprise at least 70% chondrocytes, such as at least 75%, such as at least 80%, such as at least 85%, such as at least 90%, such as at least 95%, such as at least 98%, such as at least 99%, such as 100% chondrocytes, out of the total population of cells.

In yet one embodiment, the obtained composition may comprise at least 80%, such as at least 85%, such as at least 90%, such as at least 95%, such as at least 98%, such as at least 99%, such as 100% chondrocytes, out of the total population of cells.

In another embodiment, the obtained population may be substantially free from contaminating cells. In the present context, contaminating cells may be cells other than chondrocytes, such as fibroblasts or fibroblast-like cell. In one embodiment, contaminating cells may be cells that express integrin alpha11 but not integrin alpha10.

The obtained composition may comprises highly dedifferentiated chondrocytes and fibroblastic-like cells, which may redifferentiate into chondrocytes when cultivated under optimal conditions.

"Substantially no integrin alpha11" and "substantially free from contaminating cells" have been defined herein in this disclosure.

In one embodiment, said population of high quality chondrocytes may be an integrin alpha10-enriched population of chondrocytes. Said integrin alpha10-enriched population may be obtained by a method which comprises depletion of cells expressing integrin alpha11. In one embodiment, the population of high quality chondrocytes may express substantially no integrin alpha11.

Said integrin alpha10-enriched population may be obtained by a method which comprises selecting cells expressing integrin alpha10. Cells expressing integrin alpha10 may be selected as described herein, for example by using anti-integrin alpha10 antibodies, or by other methods known to the person skilled in the art.

Said integrin alpha10-enriched population may be obtained by a method comprising cultivating the composition of chondrocytes under conditions that induce integrin alpha10 expression. Examples of such integrin alpha10 inducing conditions are found in the present disclosure. Agents that may induce integrin alpha10 expression and ascorbic acid and platelet lysate.

In one embodiment, said selection of chondrocytes having an integrin alpha10 to integrin alpha11 expression ratio of at least 4 to 1 may be conducted by isolation of chondrocytes expressing integrin alpha10. In another embodiment, said selection is achieved by depletion of chondrocytes expressing alpha11.

The isolation of a population of high quality chondrocytes may be based on procedures for separation of chondrocytes expressing integrin alpha10 from chondrocytes with substantially no expression of integrin alpha10 and/or from cells expressing integrin alpha11 but expressing no or substantially no integrin alpha10. Said separation may include magnetic separation, using e.g. antibody-coated magnetic beads and "panning" with antibody attached to a solid matrix, e.g., a plate, or other convenient techniques. Techniques providing accurate separation include fluorescence activated cell sorters, which can have varying degrees of sophistication, e.g., a plurality of color channels, light scattering detecting channels, impedance channels, etc. known to the skilled man in the art.

If an antibody or fragments thereof is used to detect the marker, it may be attached to a solid support, for example magnetic beads, to allow for a highly specific separation. The particular procedure for separation employed, e.g. centrifugation, mechanical separation, such as columns, membranes or magnetic separation, should maximize the viability of the fraction to be collected. Various techniques of different efficacy may be employed known to a person skilled in the art. The particular technique employed will depend upon efficiency of separation, cytotoxicity of the methodology, ease and speed of performance, and necessity for sophisticated equipment and/or technical skill.

In one embodiment, the population of high quality chondrocytes is isolated from a candidate composition selected from the group consisting of a cartilage tissue preparation, a tissue preparation comprising chondrocytes, a monolayer chondrocyte cell culture, and a three-dimensional chondrocyte cell culture, such as spheroids, pellets, cell sheets and chondrocytes cultured in various scaffolds.

In one embodiment, the population of high quality chondrocytes is isolated from a candidate composition derived from a cartilage tissue, a chondrocyte comprising tissue, a monolayer chondrocyte cell culture, and a three-dimensional chondrocyte cell culture, such as spheroids, pellets, cell sheets and chondrocytes cultured in various scaffolds.

In one embodiment, the method described herein may further comprise detecting expression of a secondary marker selected from the group consisting of CEP-68/CRTAC1, GP-39 cartilage glycoprotein, CD44, CD166, Collagen IIA, Collagen IIB, Aggrecan, Alizarian Red (neg), Alcian Blue, CRTAC1, CEP-68, CD49e, CD63, CD146, CD90 and Sca-1.

Induction of Integrin Alpha10 Expression in Chondrocytes

The present inventors have demonstrated an effect on proliferation and potency upon induction of integrin alpha10 expression.

Accordingly, in one aspect, the present invention concerns a method for optimizing quality and chondrocytic potency of a composition comprising chondrocytes, the method comprising inducing expression of integrin alpha10. In one embodiment, said method further comprises suppressing expression of integrin alpha11.

In another aspect, the present invention concerns a method of increasing proliferation rate of chondrocytes, the method comprising inducing expression of integrin alpha10. In one embodiment, said method further comprises suppressing expression of integrin alpha11.

In one embodiment, the induction of expression of integrin alpha10 is conducted by culturing the integrin alpha10 expressing cells in a medium comprising factors that may induce integrin alpha10 expression and/or suppress integrin alpha11.

In one embodiment, the induction of expression of integrin alpha10 may be conducted by culturing the integrin alpha10 expressing cells in a medium comprising ascorbic acid and/or platelet lysate.

In one embodiment, the integrin alpha10 to integrin alpha11 expression ratio thus obtained is at least 4 to 1, such as at least 5 to 1, such as at least 10 to 1, such as at least 15 to 1, such as at least 20 to 1, such as at least 25 to 1, such as at least 30 to 1, such as at least 35 to 1, such as at least 40 to 1, such as at least 45 to 1, such as at least 50 to 1, such as at least 60 to 1, such as at least 70 to 1, such as at least 80 to 1, such as at least 90 to 1, such as at least 100 to 1, such as at least 150 to 1, such as at least 200 to 1.

In one embodiment, the obtained integrin alpha11 expression is at the most 25% of the obtained integrin alpha10 expression, such as at the most 20% of the obtained integrin alpha10 expression, such as at the most 15% of the obtained integrin alpha10 expression, such as at the most 10% of the obtained integrin alpha10 expression, such as at the most 5% of the obtained integrin alpha10 expression, such as at the most 4% of the obtained integrin alpha10 expression, such as at the most 3% of the obtained integrin alpha10 expression, such as at the most 2% of the obtained integrin alpha10 expression, such as at the most 1% of the obtained integrin alpha10 expression, such as at the most 0.5% of the obtained integrin alpha10 expression.

It is known that integrin alpha10 expressing cells may express integrin alpha10 at different levels depending on the culture conditions they are exposed to. Hence, one way to induce integrin alpha10 expression in chondrocytes may be that of changing culture conditions, for example by changing culture medium.

Cell Preparation and Cell Culture

In one aspect, the present invention concerns an in vitro cell preparation or cell culture of chondrocytes having an integrin alpha10 to integrin alpha11 expression ratio of at least 4 to 1. In one embodiment, said integrin alpha10 to integrin alpha11 expression ratio may be at least 4, such as at least 10, such as at least 15, such as at least 20, such as at least 25, such as at least 30, such as at least 35, such as at least 40, such as at least 45, such as at least 50, such as at least 60, such as at least 70, such as at least 80, such as at least 90, such as at least 100. In another embodiment, said integrin alpha10 to integrin alpha11 expression ratio may be below 200, such below 150, such as below 100.

In one aspect, the present invention concerns an in vitro cell preparation or cell culture of chondrocytes wherein the integrin alpha11 expression is at the most 25% of the integrin alpha10 expression, such as at the most 20% of the integrin alpha10 expression, such as at the most 15% of the integrin alpha10 expression, such as at the most 10% of the integrin alpha10 expression, such as at the most 5% of the integrin alpha10 expression, such as at the most 4% of the integrin alpha10 expression, such as at the most 3% of the integrin alpha10 expression, such as at the most 2% of the integrin alpha10 expression, such as at the most 1% of the integrin alpha10 expression, such as at the most 0.5% of the integrin alpha10 expression.

In one embodiment, the present invention concerns an integrin alpha10-enriched population of chondrocytes isolated from the cell preparation/culture with an anti-integrin alpha10 antibody and an anti-integrin alpha11 antibody.

In one embodiment, said enriched population of chondrocytes may be obtained by selecting chondrocytes with a high expression of integrin alpha10 or inducing integrin alpha10 expression. In another embodiment, said enriched population of chondrocytes may be obtained by depletion of highly dedifferentiated chondrocytes or fibroblastic-cells with expression of integrin alpha11 or suppressing integrin alpha11 expression.

In one embodiment, the enriched population may have an integrin alpha10 to integrin alpha11 expression ratio of at least 4 to 1, such as at least 5 to 1, such as at least 10 to 1, such as at least 15 to 1, such as at least 20 to 1, such as at least 25 to 1, such as at least 30 to 1, such as at least 35 to 1, such as at least 40 to 1, such as at least 45 to 1, such as at least 50 to 1, such as at least 60 to 1, such as at least 70 to 1, such as at least 80 to 1, such as at least 90 to 1, such as at least 100 to 1, such as at least 150 to 1, such as at least 200 to 1.

In one embodiment, the enriched population may have an integrin alpha11 expression of at the most 25% of the integrin alpha10 expression, such as at the most 20% of the integrin alpha10 expression, such as at the most 15% of the integrin alpha10 expression, such as at the most 10% of the integrin alpha10 expression, such as at the most 5% of the integrin alpha10 expression, such as at the most 4% of the integrin alpha10 expression, such as at the most 3% of the integrin alpha10 expression, such as at the most 2% of the integrin alpha10 expression, such as at the most 1% of the integrin alpha10 expression, such as at the most 0.5% of the integrin alpha10 expression.

Use of the Described Methods

In one aspect, the current invention concerns use any one of the methods described herein, for
a) quality assuring chondrocyte compositions;
b) monitoring consistency and/or reproducibility of chondrocyte compositions;
c) predicting potency, hence function, of chondrocyte compositions and cultures;
d) in-process control chondrocyte compositions
e) in-process control of expansion of chondrocyte compositions;
f) conducting release test of chondrocyte compositions;
g) conducting a potency assay of chondrocyte composition; and/or
h) prediction of clinical outcome of chondrocyte compositions.

Hence, in one embodiment, the method for determining quality of a composition comprising chondrocytes comprising the steps of:
a) providing a candidate composition comprising chondrocytes;
b) analyzing the expression levels of integrin alpha10 and integrin alpha11 in said composition;
c) comparing the expression level of integrin alpha10 to the expression level of integrin alpha11,
wherein an integrin alpha10 to integrin alpha11 expression ratio of at least 4 to 1 is indicative of
    chondrocytic identity of the chondrocytes in the chondrocyte composition,
    differentiated state of the chondrocytes in the chondrocyte composition,
    purity of the chondrocyte composition, and/or
    potency of the chondrocytes of the chondrocyte composition,
may be used to quality assure a chondrocyte composition.

Hence, in one embodiment, the present disclosure relates to use of a method for determining quality of a composition comprising chondrocytes comprising the steps of:
a) providing a candidate composition comprising chondrocytes;
b) analyzing the expression levels of integrin alpha10 and integrin alpha11 in said composition;
c) comparing the expression level of integrin alpha10 to the expression level of integrin alpha11,
wherein an integrin alpha10 to integrin alpha11 expression ratio of at least 4 to 1 is indicative of
    chondrocytic identity of the chondrocytes in the chondrocyte composition,
    differentiated state of the chondrocytes in the chondrocyte composition,
    purity of the chondrocyte composition, and/or
    potency of the chondrocytes of the chondrocyte composition,
for quality assuring and/or quality controlling a chondrocyte composition.

In one embodiment, the present disclosure relates to use of a method for determining quality of a composition comprising chondrocytes comprising the steps of:
a) providing a candidate composition comprising chondrocytes;
b) analyzing the expression levels of integrin alpha10 and integrin alpha11 in said composition;
c) comparing the expression level of integrin alpha10 to the expression level of integrin alpha11,
wherein an integrin alpha10 to integrin alpha11 expression ratio of at least 4 to 1 is indicative of
    chondrocytic identity of the chondrocytes in the chondrocyte composition,
    differentiated state of the chondrocytes in the chondrocyte composition,
    purity of the chondrocyte composition, and/or
    potency of the chondrocytes of the chondrocyte composition, for in-process control of chondrocyte compositions and/or expansion of chondrocyte compositions.

In one embodiment, the present disclosure relates to use of a method for determining quality of a composition comprising chondrocytes comprising the steps of:
a) providing a candidate composition comprising chondrocytes;
b) analyzing the expression levels of integrin alpha10 and integrin alpha11 in said composition;
c) comparing the expression level of integrin alpha10 to the expression level of integrin alpha11,
wherein an integrin alpha10 to integrin alpha11 expression ratio of at least 4 to 1 is indicative of
　chondrocytic identity of the chondrocytes in the chondrocyte composition,
　differentiated state of the chondrocytes in the chondrocyte composition,
　purity of the chondrocyte composition, and/or
　potency of the chondrocytes of the chondrocyte composition,
for conducting release test of chondrocyte compositions.

In one embodiment, the present disclosure relates to use of a method for determining quality of a composition comprising chondrocytes comprising the steps of:
a) providing a candidate composition comprising chondrocytes;
b) analyzing the expression levels of integrin alpha10 and integrin alpha11 in said composition;
c) comparing the expression level of integrin alpha10 to the expression level of integrin alpha11,
wherein an integrin alpha10 to integrin alpha11 expression ratio of at least 4 to 1 is indicative of
　chondrocytic identity of the chondrocytes in the chondrocyte composition,
　differentiated state of the chondrocytes in the chondrocyte composition,
　purity of the chondrocyte composition, and/or
　potency of the chondrocytes of the chondrocyte composition,
for conducting a potency assay of a chondrocyte composition.

EXAMPLES

Figure 1B:
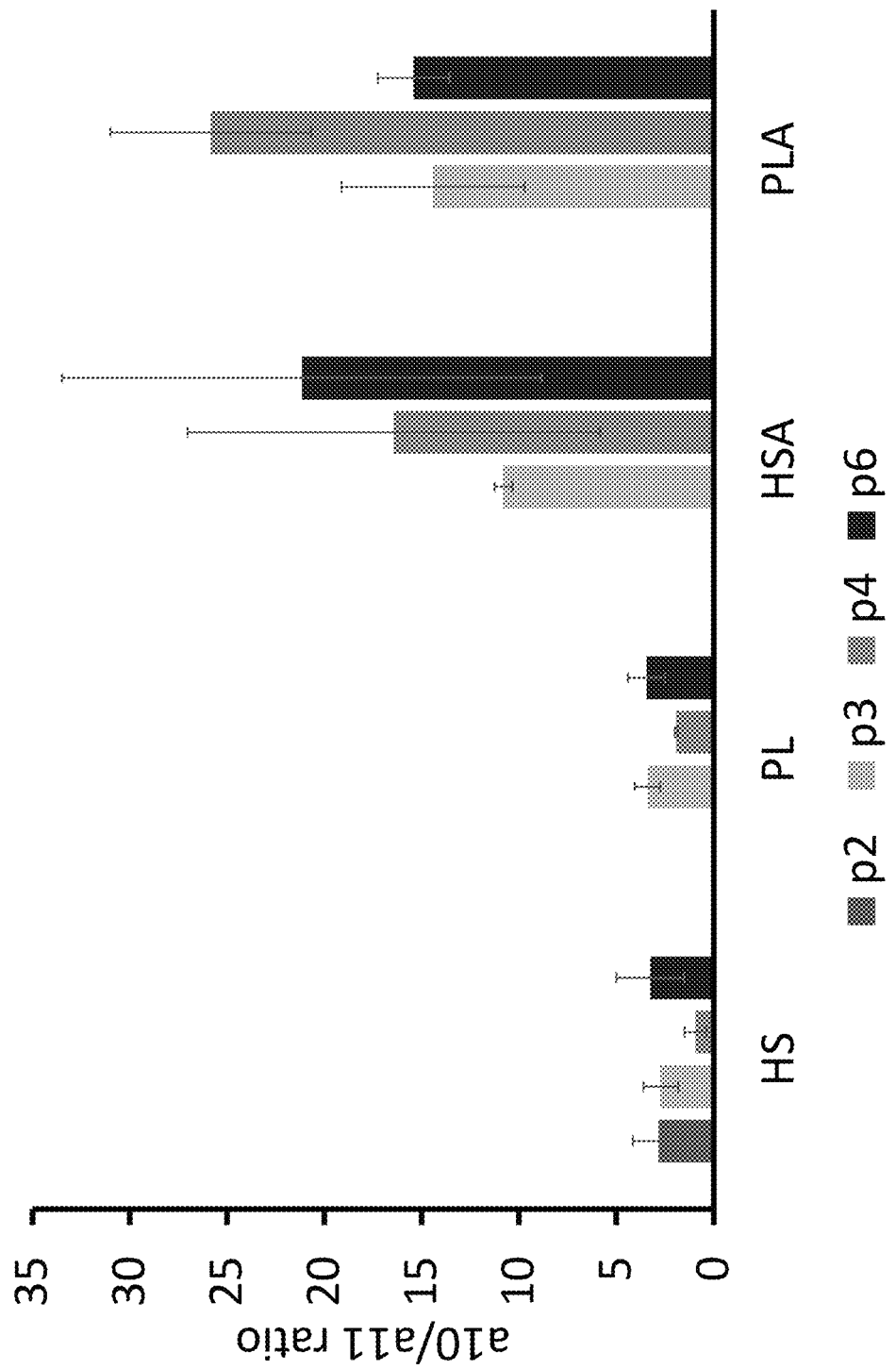
FIG. 1B. Flow cytometry analysis of four human chondrocyte preparations, 853, 854, 875, and 876, cultured in human serum (HS), platelet lysate (PL) with or without ascorbic acid (A) for 2-6 passages. Passage 2 cells were cultured only in HS. The results show the mean±SEM ratio of integrin alpha10/integrin alpha11 (n=2-4). The addition of ascorbic acid (A) has a pronounced and immediate effect in changing the alpha10/alpha11 ratio in favor of alpha10. This effect is evident irrespective the use of HS or PL.

Example 1: Expression of Integrin alpha10beta1 and Integrin alpha11beta1 on Chondrocytes Cultured in Human Serum (HS) or Platelet Lysate (PL), with or without Addition of Ascorbic Acid Chondrocytes from four different preparations, 853, 854, 875 and 876 were cultured in the presence of 10% HS in DMEM or 5% PL in DMEM with or without ascorbic acid (50 µg/ml). Integrins alpha10beta1 and alpha11beta1 expressions were analyzed after passage 2, 3, 4 and 6 by flow cytometry, using the following monoclonal antibodies: alpha10 antibody directly conjugated to phycoerythrin (PE) and alpha11 antibody directly conjugated to Alexa Fluor A647 (Xintela AB) diluted in FACS buffer (PBS, 1% FBS, 0.1% NaN$_3$), was added (1 µg/mL).
Conclusion:

The analysis demonstrated that surface expression of integrin alpha10beta1 decreased with passages on chondrocytes cultured in the presence of HS alone. When the chondrocytes were cultured in the presence of PL, the surface expression of integrin alpha10 increased, and remained high over all six passages. FIG. 1A shows results from chondrocyte preparations 853 and 854. Addition of ascorbic acid to the culture medium maintained and unexpectedly even increased the expression of integrin alpha10beta1 in the HS cultures, especially at later passages, but did not alter the already high expression of integrin alpha10beta1 on chondrocytes cultured in PL (FIG. 1A). The flow cytometry analysis unexpectedly showed that addition of ascorbic acid to the media decreased expression of integrin alpha11beta1, which thus increased the integrin alpha10beta1/integrin alpha11beta1 ratio. This effect was seen both in the HS and PL cultures in the presence of ascorbic acid as illustrated (FIG. 1B) where results from the chondrocyte preparations, 853, 854, 875 and 875, are summarised.

Example 2: Growth Kinetics and Evaluation of Different Culture Conditions

Figure 2:
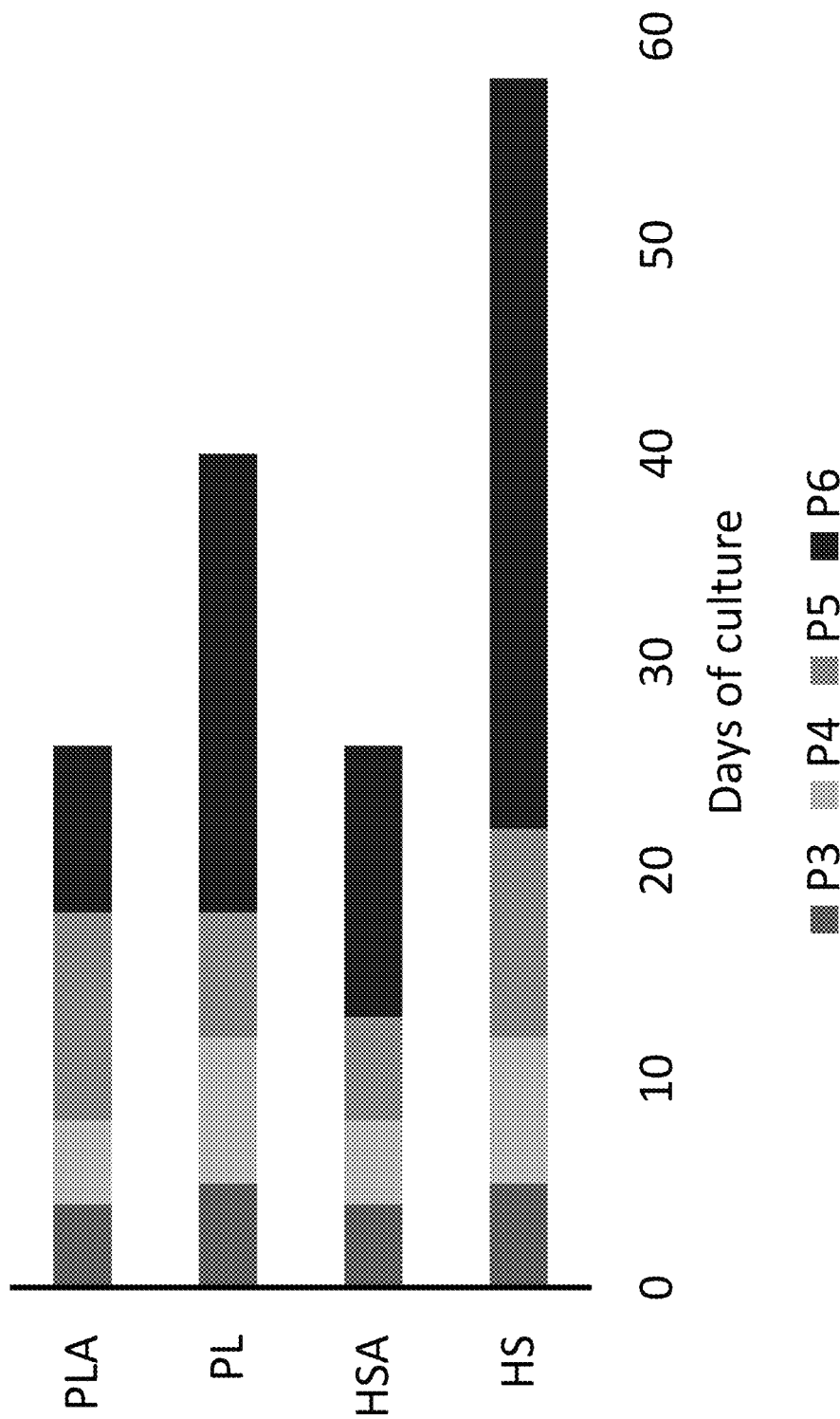
FIG. 2. Growth kinetic analysis showing cell culture time to reach confluency in passages 3-6 for 853 chondrocytes cultured in human serum (HS), HS with ascorbic acid (HSA), platelet lysate (PL) or PL with ascorbic acid (PLA). The addition of ascorbic acid (A) and PL, especially A, had a pronounced effect on the chondrocyte proliferation.

Relationship between specific growth rate of the chondrocytes and different culture medium was investigated. For this purpose chondrocytes from preparation 853 were cultured in medium containing only HS up to passage 2. After passage 2 cells were cultured in HS or PL in the absence or in the presence of ascorbic acid. When the cells reached 80% confluency, cells were harvested, counted and re-seeded at the same density.
Conclusion:

Ascorbic acid and PL increase proliferation rate of chondrocytes. In the presence of ascorbic acid, cells proliferated faster in each passage compared to media lacking ascorbic acid (FIG. 2). This was seen both in medium containing HS and PL. The effect was more prominent in the later passages (5-6) than in earlier passages. In the absence of ascorbic acid, the chondrocytes needed longer time to reach confluency. PL also increased proliferation compared to HS.

Example 3. Impact of Different Culture Conditions During Monolayer Expansion on the Quality and Potency of Chondrocytes To investigate if culture conditions, known to change the expression of integrins alpha10beta1 and alpha11beta1 during expansion of chondrocytes will affect the chondrocyte quality and potency (redifferentiation capacity), the following experiments were performed.

Chondrocytes from preparations 853, 854, 875 and 876 were cultured for four passages in HS, HSA or PLA and then transferred to pellet mass cultures. In addition, samples of the different chondrocyte cultures were analyzed for integrin alpha10beta1-expression by flow cytometry and Q-PCR right before the start of the pellet mass culture.
Q-PCR Chondrocyte mRNA was isolated using RNeasy Mini Kit (Qiagen, Germany) and cDNAs were synthesized from high quality total RNAs samples, normalized and validated with GAPDH in two sequential qPCR analyses. The real-time PCR detection of integrin alpha10 was conducted using gene specific primers and TaqMan probe (gene expression assay HS00174623_m1, and Hs02758991_g1 from Life Technology) and run as recommended by the manufactures. The detection system was StepOne Plus (Applied Biosystems). Integrin alpha10 expression was normalized against control GAPDH and relative quantification values (RQ) of integrin alpha10 was calculated.
Pellet Mass Culture Chondrocytes were cultured in monolayer in culture medium (alpha-Minimum Essential Medium (alpha-MEM) and Ham's F12 from Biochrom, 1:1 proportion) with 3 mM glutamin, HS (10%) or PL (5%) with or without L-Ascorbic acid 2-phosphate-sesquimagnesium salt hydrate (A) and antibiotic-antimycotic. After passage 4, cells were detached centrifuged, and resuspended in TIDA medium (DMEM F12 with high glucose (4.5 g/L no phenol red), antibiotic-antimycotic (1×), TGFbeta1 (13 ng/ml), Insulin/Transferin/Selenium (ITS-X; 1×), Dexamethasone (10 nM), A (50 µg/ml) and HS (2%)). Samples containing 200000 cells were transferred into 14 ml falcon tube and cell suspensions were centrifuged to form a pellet. The cell pellets were subsequently cultured under hypoxic conditions (4% O2, 5% CO2 and 95% humidity) for 1-4 weeks and then analysed by immunohistochemistry (IHC).

Immunohistochemistry

The chondrocyte pellets were embedded in TissueTek and frozen. Sections were collected on slides and immunolabelled with primary monoclonal antibodies (anti-collagen I, anti-collagen II or anti-alpha10 integrin and then with secondary antibodies anti-mouse-HRP (polymers, DAKO).

Figure 3A:
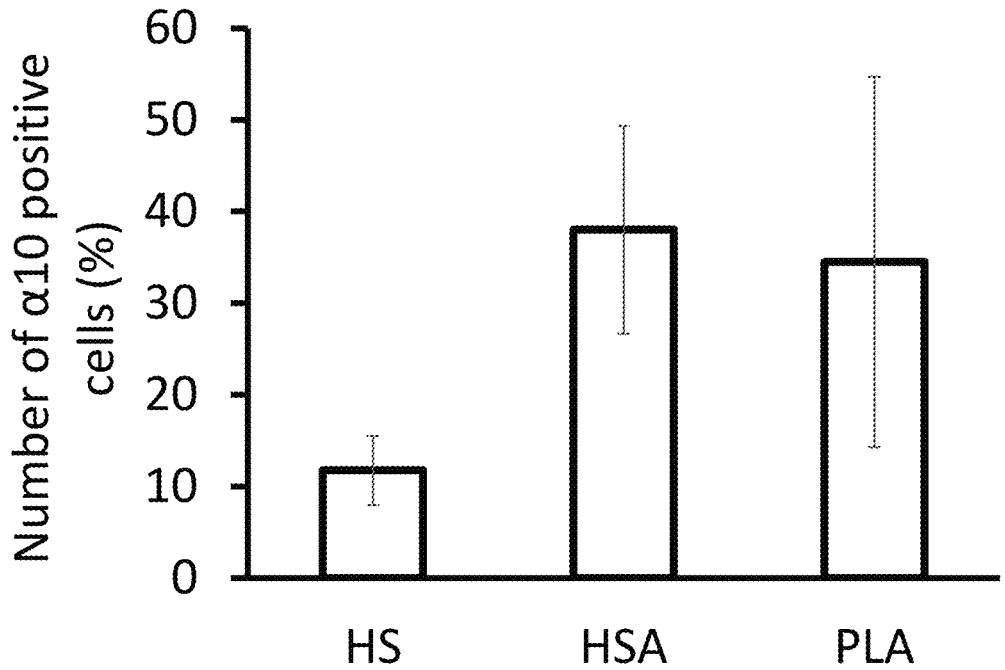
FIG. 3A. Flow cytometry analysis of alpha10beta1 on human chondrocyte preparations 853, 854, 875 and 876, cultured in human serum (HS), human serum with ascorbic acid (HSA) or platelet lysate with ascorbic acid (PLA). The Integrin alpha10beta1-(alpha 10) expression is shown as mean±SEM of the four chondrocyte preparations. These cells were used in the differentiation experiments in FIG. 4.
Figure 3B:
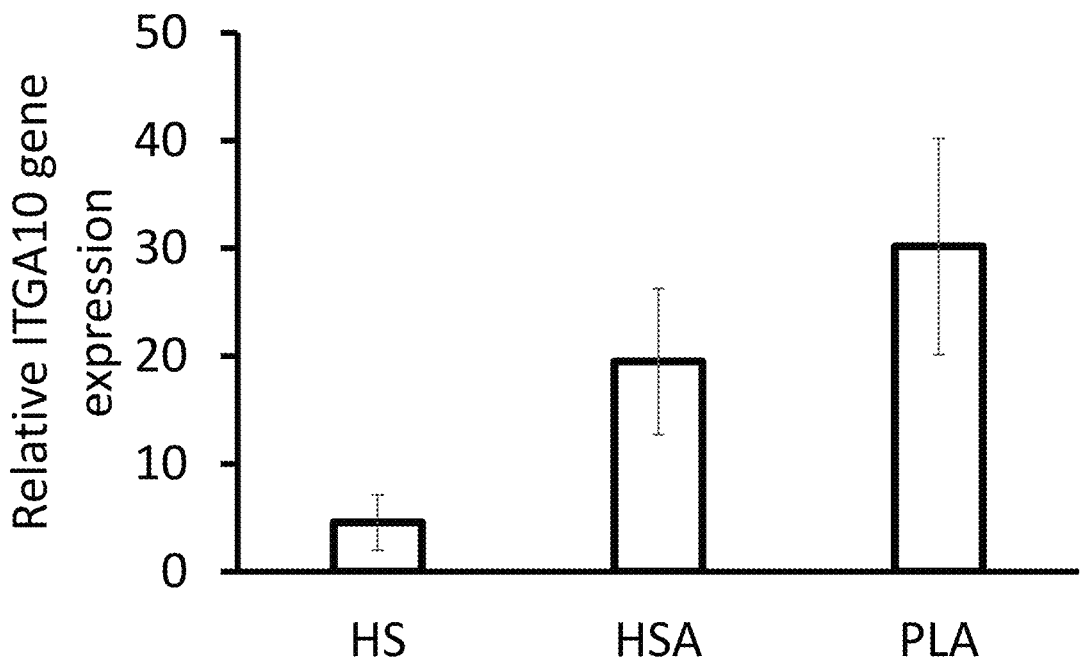
FIG. 3B. Gene expression analyses of ITGA10 on human chondrocyte preparations 853, 854, 875 and 876, cultured in human serum (HS), human serum with ascorbic acid (HSA) or platelet lysate with ascorbic acid (PLA). Relative ITGA10 gene expression is shown as mean±SEM for the four cell lines. GAPDH was used as a house-keeping gene for control.

Conclusion (I):

The results after the monolayer culture corroborated the findings from example 2, showing that PL and ascorbic acid induced expression of integrin alpha10 and clearly increased the integrin alpha10beta1-expression on chondrocytes during monolayer cultures, as compared to HS only. The flow cytometry data (FIG. 3A) indicated an increase in alpha10beta1-expression when using PL and HS with ascorbic acid (FIG. 3A). Similar results were seen at the gene expression level, as represented by the integrin alpha10 gene transcript, ITGA10 (FIG. 3B).

Figure 4A:
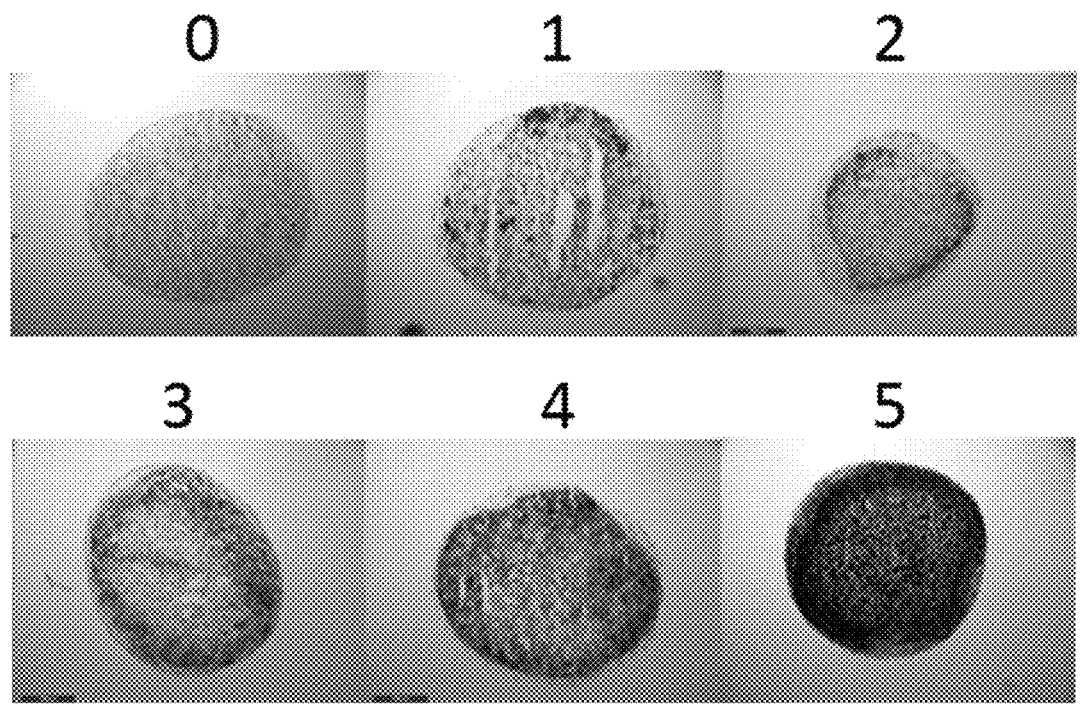
FIG. 4A. Evaluation score system of collagen II-expression in tissue section of chondrocyte pellets as analyzed by immunohistochemistry. The degree of collagen II-expression was scored in a 0-5 scale.
Figure 4B:
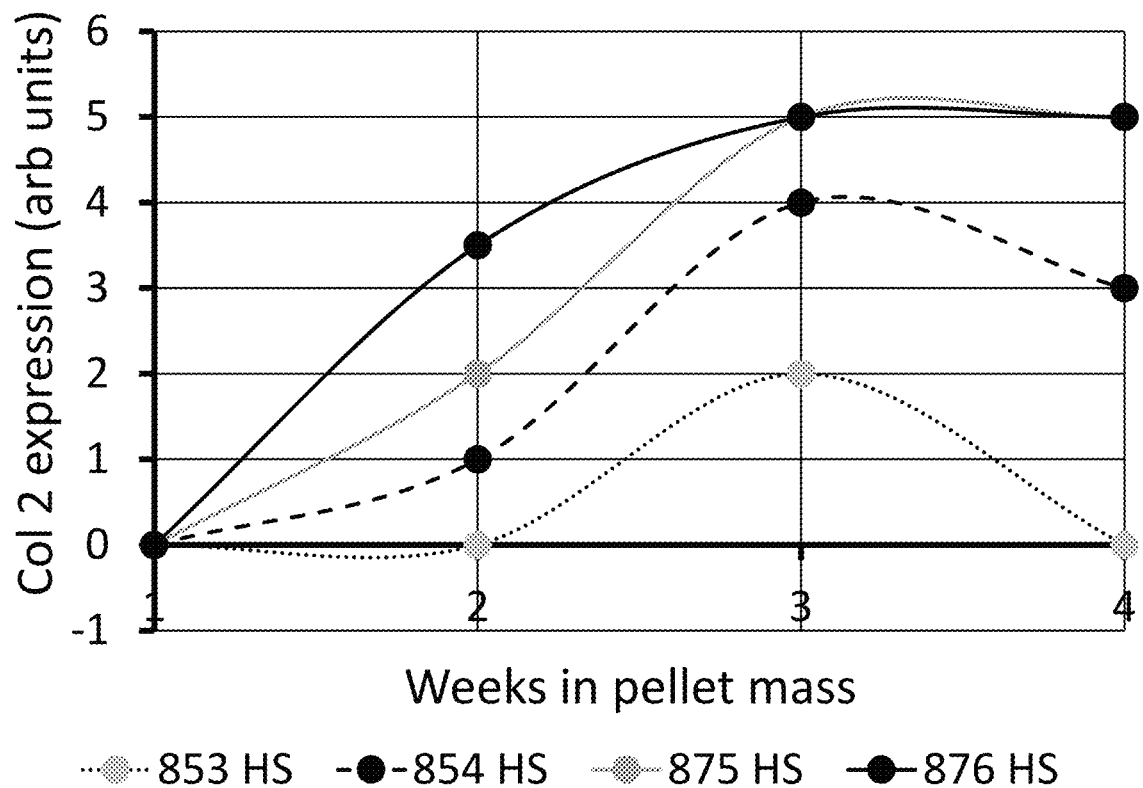
FIG. 4B. A summary of the collagen type II (Col2) expression scores for the human chondrocyte preparations 853, 854, 875 and 876, expanded in HS and grown in pellet mass cultures for 1-4 weeks in the presence of the rediffeentiation media TIDA.

In order to evaluate the quality and the potency of the chondrocytes in the pellet mass cultures, a scoring system based on immunohistochemical analysis of expression of the cartilage specific collagen type II was established. The score representing increasing collagen type II-expression has a nominal range from 0-5 (FIG. 4A).

The collagen type II-scores for the various culture conditions—HS, HSA and PLA—are summarized in FIG. 4. These results showed a large variation in the collagen type II-expression (redifferentiation/potency) between the different chondrocyte preparations, when the cells were cultured in HS (FIG. 4B). Chondrocytes preparation 853 showed a low expression of collagen type II at all times, whereas 876 showed some collagen type II-expression already after one week, and high expression after three weeks.

Figure 4C:
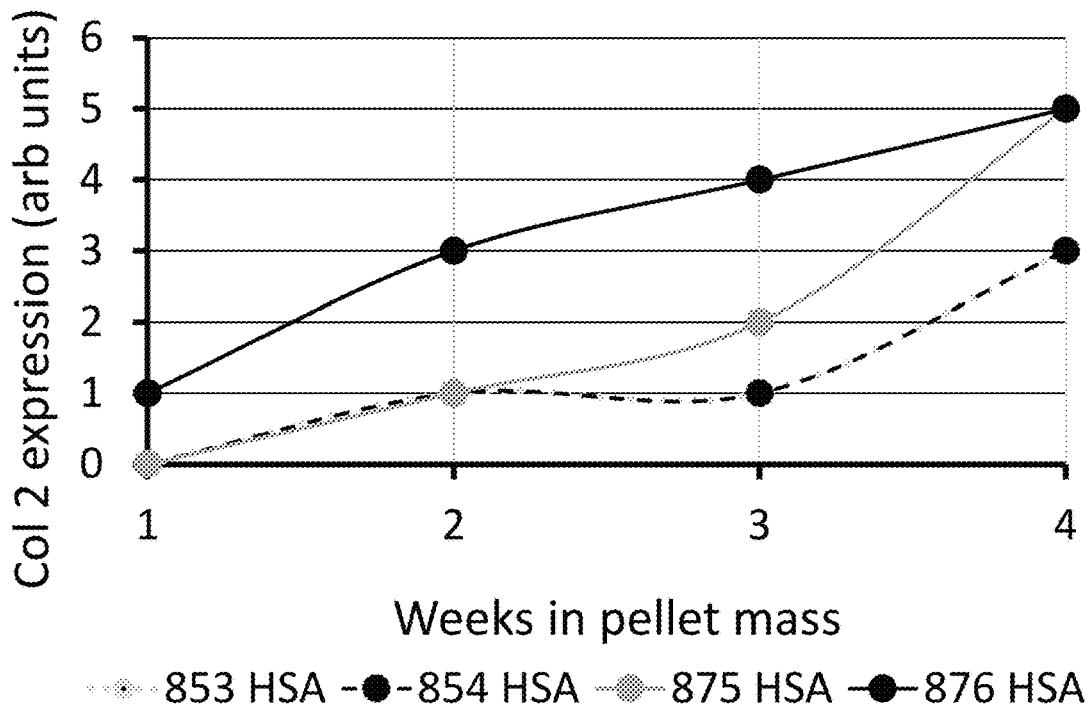
FIG. 4C. A summary of the collagen type II (Col2) expression scores for the human chondrocyte preparations 853, 854, 875 and 876, expanded in HSA and grown in pellet mass cultures for 1-4 weeks in the presence of the rediffeentiation media TIDA.
Figure 4D:
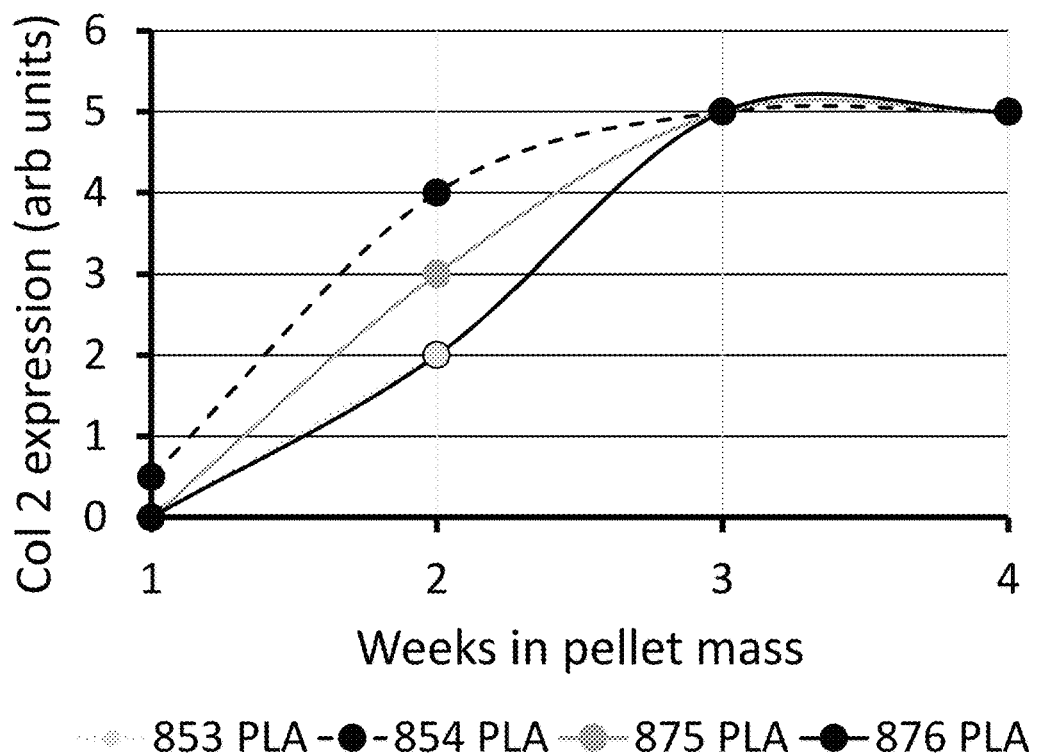
FIG. 4D. A summary of the collagen type II (Col2) expression scores for the human chondrocyte preparations 853, 854, 875 and 876, expanded in PLA and grown in pellet mass cultures for 1-4 weeks in the presence of the rediffeentiation media TIDA.

Chondrocytes cultured in HSA (HS with ascorbic acid) demonstrated a non-uniform behavior with respect to collagen type II-expression. Chondrocytes from preparation 875 and 876 showed high collagen type II-expression after four weeks, while 853 and 854 did not reach a high score during the four-week assay (FIG. 4C). When the cells were cultured in PLA, on the other hand, all chondrocyte preparations followed a uniform pattern of collagen type II expression. The expression of collagen type II increased rapidly and all four chondrocyte preparations reached the highest score already after 3 weeks. (FIG. 4D).

To investigate a possible correlation between the integrin alpha10beta1-expression on the chondrocytes after monolayer expansion in HS and their potency (redifferentiation potential), as judged by collagen type II-expression in pellet mass cultures (week two and three), we performed a Pearson correlation analysis on chondrocytes from 9 individual preparations, (803, 811, 816, 842, 853, 854, 875, 876 and 914), cultured in HS.

Figure 5:
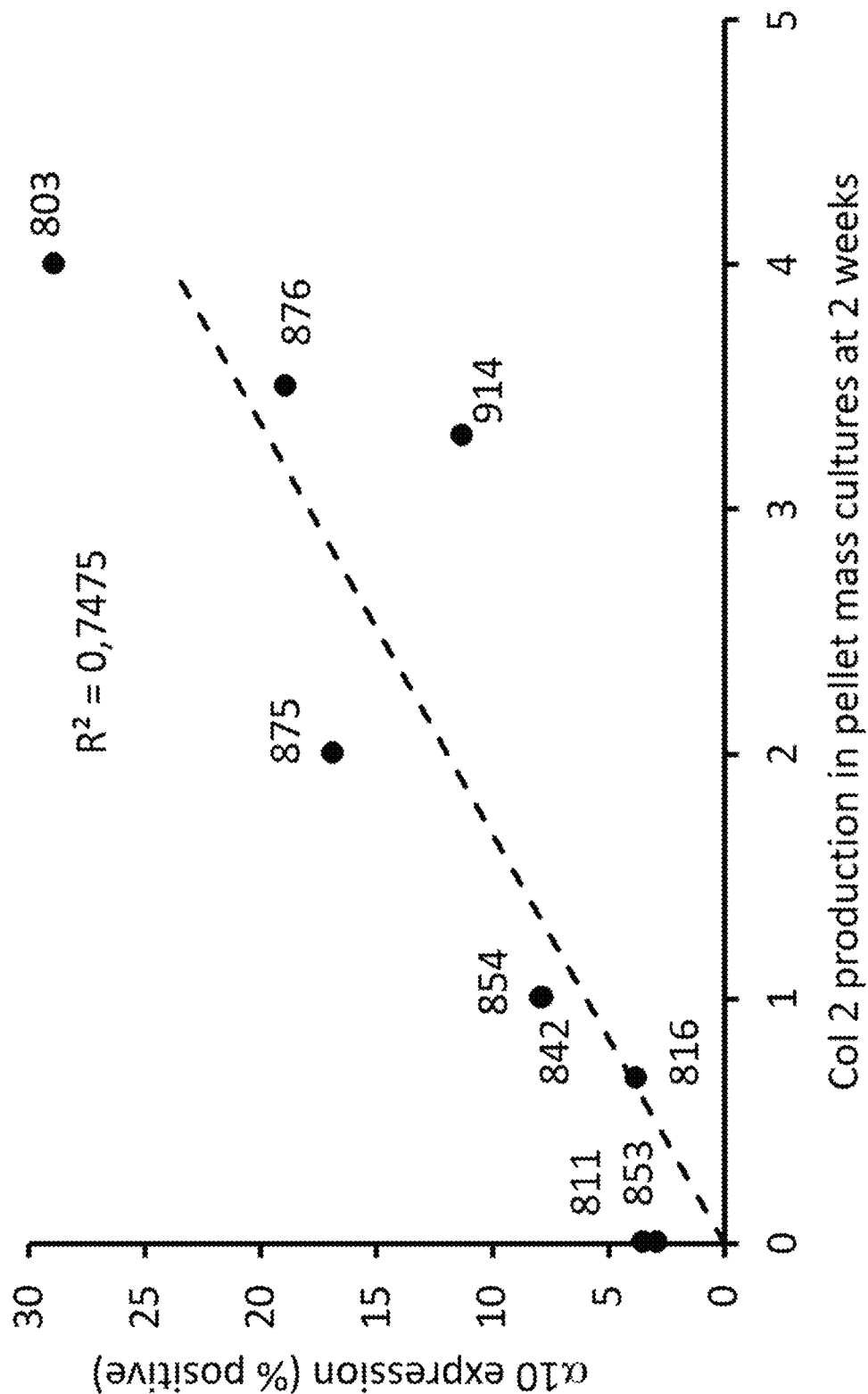
FIG. 5. Correlation between the integrin alpha10beta1-expression (flow cytometry) on the human chondrocyte preparations 853, 854, 875, 876, 803, 811, 816, 842 and 914 cultured in monolayer in HS and the collagen type II-expression (immunohistochemistry) after 2 weeks in pellets mass cultures. Pearson correlation analysis demonstrated a high level of correlation, with a coefficient ($R^2$) of 0.75. If sample 914, which can be considered an outlier, is omitted, an $R^2$ of 0.93 is achieved (data not shown).

FIG. 5 illustrates a high degree of correlation between integrin alpha10beta1-expression level on monolayer cultured chondrocytes and their collagen type II producing capacity in pellet mass cultures ($R^2$ value of 0.75 after 2 weeks). This demonstrates that integrin alpha10beta1 is a marker of chondrocyte quality and can predict potency of chondrocytes.

Furthermore, to investigate a possible correlation between the integrin alpha10 to integrin alpha11 expression ratio (alpha10alpha11 ratio) on chondrocytes after monolayer expansion in HS and their potency (redifferentiation capacity), as judged by collagen type II-expression in pellet mass cultures (week two and three), we analyzed the alpha10/alpha11 ratio on chondrocytes with low (811) and high (803) rediffeentiation capacity.

Figure 8A:
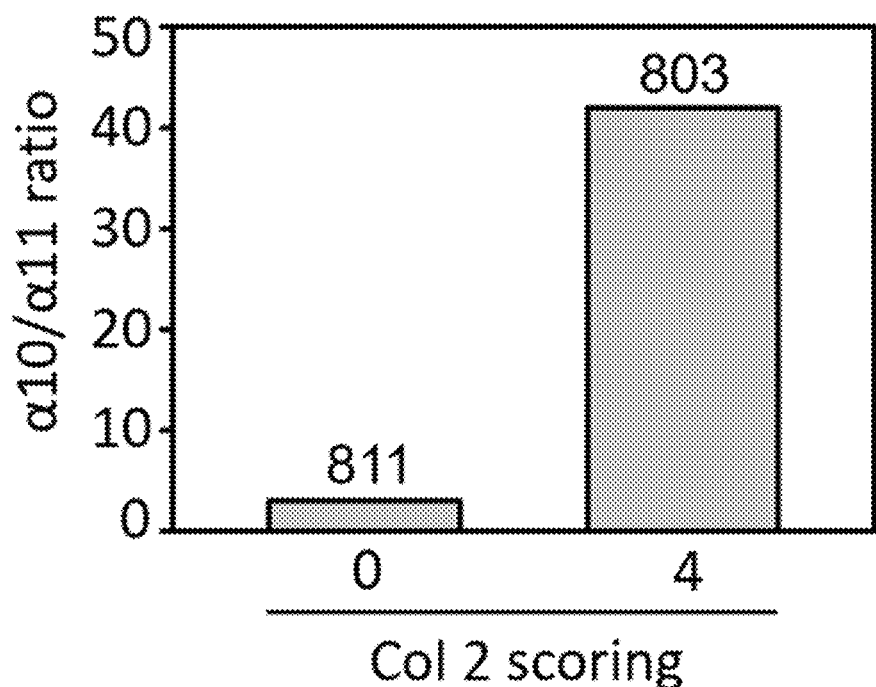
FIG. 8A. Expression of integrins alpha10($\alpha$10) and alpha11($\alpha$11) was analysed on monolayer cultured human chondrocytes from samples 803 and 811 prior to pellet mass cultures. Flow cytometry analysis showed low integrin $\alpha$10/integrin $\alpha$11 ratio in sample 811 and high integrin $\alpha$10/integrin $\alpha$11 ratio in sample 803.
Figure 8B:
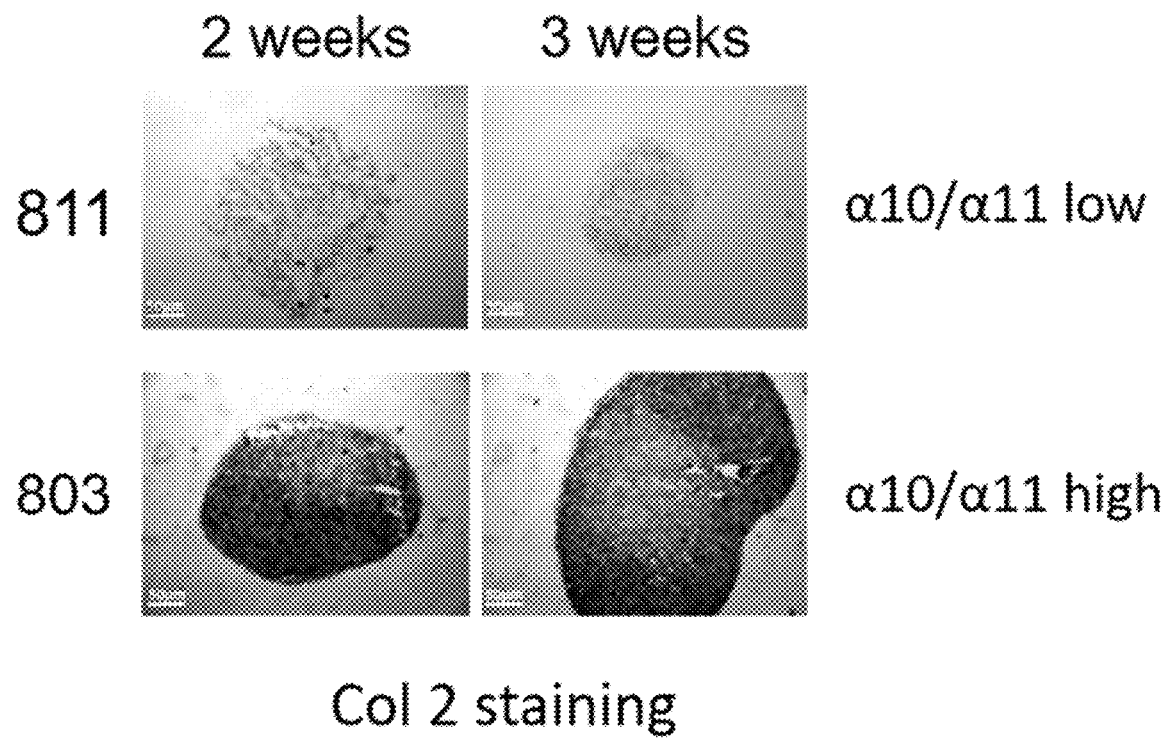
FIG. 8B. Histologic evaluation of Col2 production in chondrocyte from samples 803 and 811 cultured in pellet mass for 2 and 3 weeks. Tissue sections from the chondrocyte pellets were analysed for expression of collagen type II (Col2) and the degree of Col2 expression was scored in a 0-5 scale. The results show no/very low expression of Col2 in pellets from chondrocytes 811 and high expression of Col2 in pellets from chondrocytes 803.

FIG. 8 demonstrates that a chondrocyte preparation with low alpha10/alpha11 ratio (811) have low redifferentiation cacity while chondrocyte preparation with high alpha10alpha11 ratio (803) have high redifferentiation cacity. This demonstrates that i alpha10/alpha11 ratio can be used to determine chondrocyte quality and can predict potency of chondrocytes and in particular chondrocytic identity and differentiated state of the chondrocytes in the chondrocyte composition.

Conclusion (II):

The results show that integrin α10/integrin α11 ratio on chondrocyte in monolayer cultures correlate with expression of Col-II in subsequent pellet mass cultures (FIG. 8). This demonstrates that the ratio of integrin α10/integrin α11 can be used to predict the redifferentiation potential and function of cultured chondrocytes and determine differentiated state and functional potency of the chondrocytes of the chondrocyte composition.

Example 4. Pellet Mass Culture Showing Integrin alpha10beta1 and Integrin alpha11beta1 Co-Localization with Collagen Types II and I, Respectively In order to demonstrate that the markers integrin alpha10beta1 and integrin alpha11beta1 co-localizes with cartilage and fibrous collagens, respectively, we investigated the protein expression pattern by IHC and Immunofluorescence. We used pellets originated from chondrocyte preparation 875, expanded in monolayer in PL with ascorbic acid (PLA) and subsequently cultured for two weeks in pellet mass culture in the presence of TIDA differentiation medium. The pellets were analyzed by IHC (FIG. 6A) and immunofluorescence (FIG. 6B) to demonstrate the expression pattern of the integrins and the collagens.

Immunofluorescence Procedure

Chondrocyte pellets were embedded in TissueTek (Sakura, Jpn) and frozen on dry ice. Sections, 8 µm (made in a MICROM HM 500 OM cryostat), were collected on SuperFrost Plus slide and used for immunolabelling with primary antibodies mixed with antibodies made against other antigens and with fluorophore conjugated secondary Ab/Abs.

Secondary antibodies for multiple labelling (highly affinity purified, mainly Fab2 fragments) were made in donkey or in goat against rabbit, mouse, or goat IgG's or against chicken IgY, diluted in PBS containing 1% BSA. For simultaneous fluorescence visualization of two epitopes the primary and secondary are applied as a mixture.

Figure 6A:
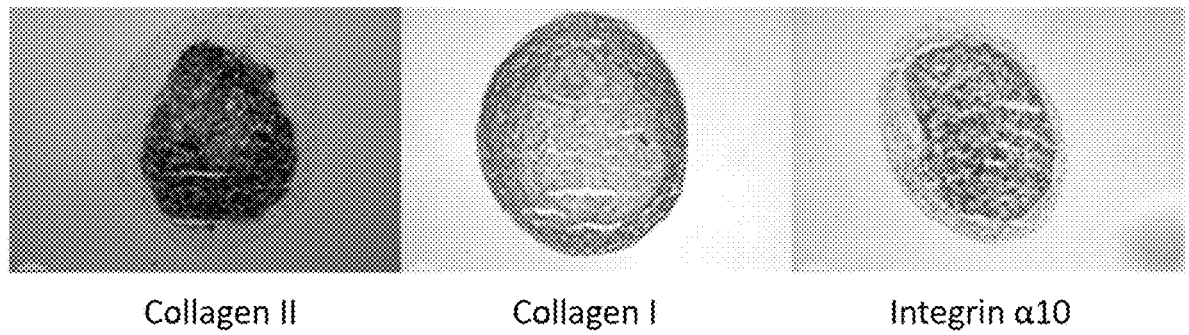
FIG. 6A. Immunohistochemical analysis of collagen II, collagen I and integrin alpha10beta1 on chondrocyte preparation 875 grown in monolayer in PLA and then for two weeks in pellet culture with the rediffeentiation media TIDA. Integrin alpha10beta1 was found to colocalise with collagen type II while collagen type I was mainly expressed in the outer region where integrin alpha10beta1 was low or absent.
Figure 6B:
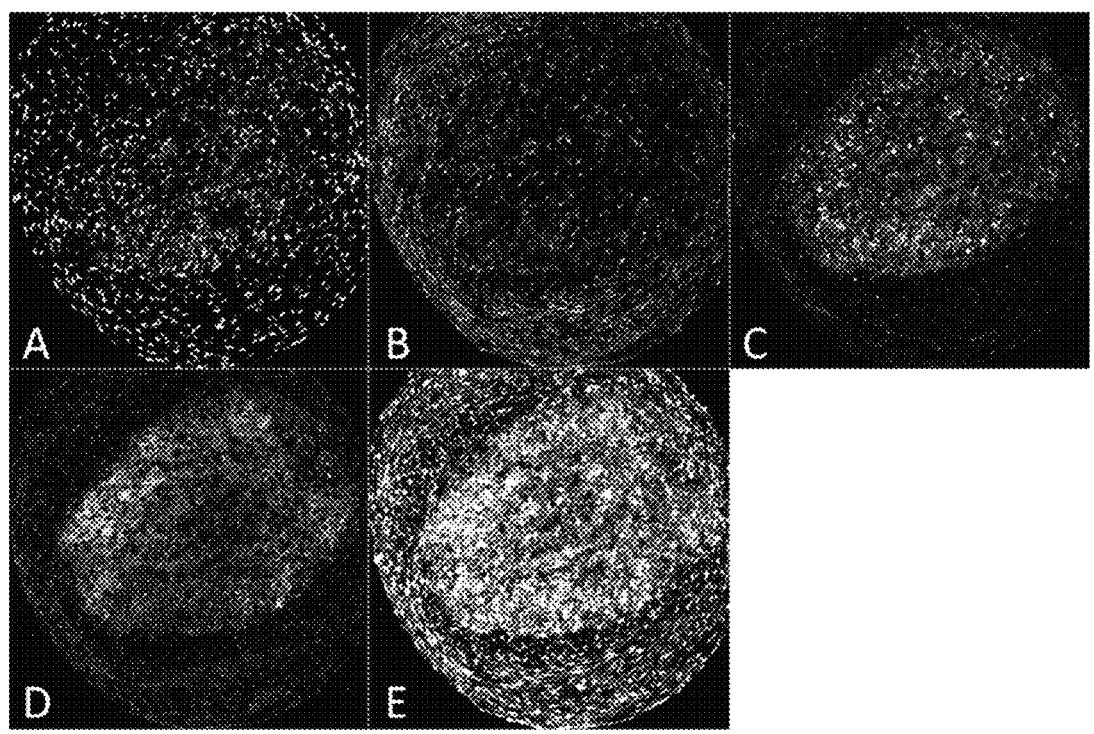
FIG. 6B. Immunofluorescence staining of integrin alpha11beta1 (B) integrin alpha10beta1 (C), collagen II (D), and) on 875 chondrocytes cultured in monolayer in PLA and then for two weeks in pellet culture with TIDA. DAPI staining of the nucleus is shown in (A) and a merged picture of the different staining in (E). The stainings were visualised by confocal microscopy. Scale bars 50 μm. Integrin alpha10beta1 was found to colocalise with collagen type II while integrin alpha11beta1 is expressed in the outer region of the pellet where expression of collagen type I is found (see FIG. 6A).

Conclusion: The IHC staining shows that integrin alpha10beta1 clearly co-localized with collagen type II in the central region of the pellet whereas collagen I is mainly found in the outer part of the pellet where integrin alpha10beta1 is absent or low (FIG. 6A). Using immunofluorescence we confirmed clear co-localization between integrin alpha10beta1 and collagen II and furthermore that integrin alpha11beta1 is mainly present on cells in the collagen I rich outer part of the pellet (FIG. 6B).

Example 5. Integrin alpha10beta1 and Integrin alpha11beta1 Flow Cytometry Analysis to Determine Purity and Quality of Chondrocyte Preparations In order to evaluate the feasibility of assessing expression of integrin alpha10beta1 and integrin alpha11beta1 to determine identity and purity as a quality assay of chondrocyte preparations, a combination of chondrocytes and fibroblast-like synoviocytes was used. Different amounts of fibroblast-like synoviocytes were added to a chondrocyte preparation and integrins alpha10beta1 and alpha11beta1 were analyzed by flow cytometry. Fibroblast-like synoviocytes from healthy subjects (HFLS) and osteoarthritis patients (HFLS-OA), as well as chondrocytes from preparation 875 and chondrocytes from human nasal cartilage (HNC), were used. To investigate the sensitivity of the assay, increasing amounts of synoviocytes (HFLS-OA) were added to HNC cells ranging from 0.5% to 100% of HFLS-OA.

Figure 7A:
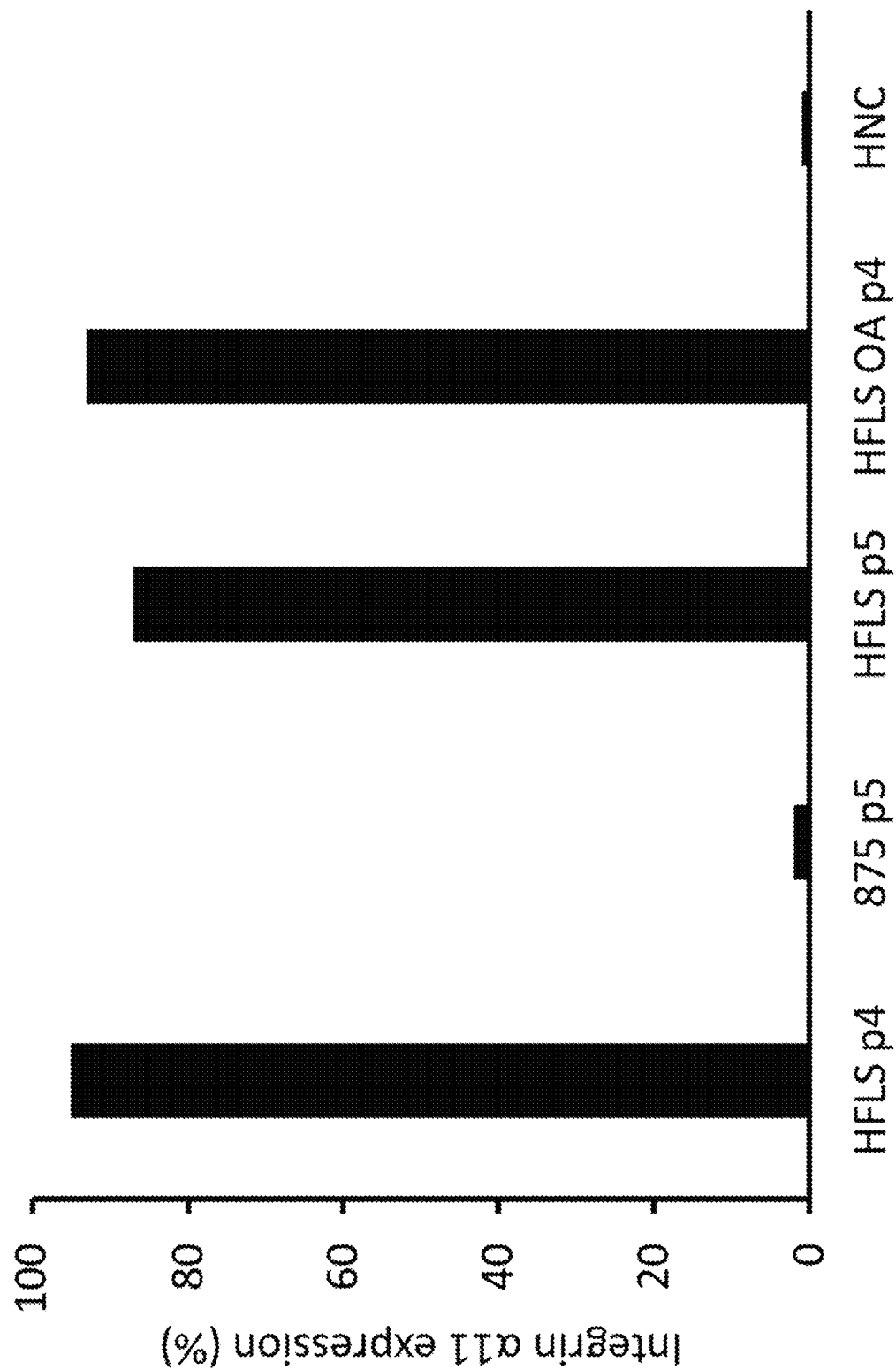
FIG. 7A. Flow cytometry analysis of integrin alpha11 beta1 (X-axis) on human fibroblast-like synoviocytes (HFLS), chondrocyte preparation 875, HFLS-OA (fibroblast-like cells s from osteoarthritis patient) and human nasal chondrocytes (HNC). The results show that integrin alpha11beta1 is expressed on the fibroblast-like cells but not on chondrocytes. Side scatter (SSC-A) is shown on the Y axis.
Figure 7B:
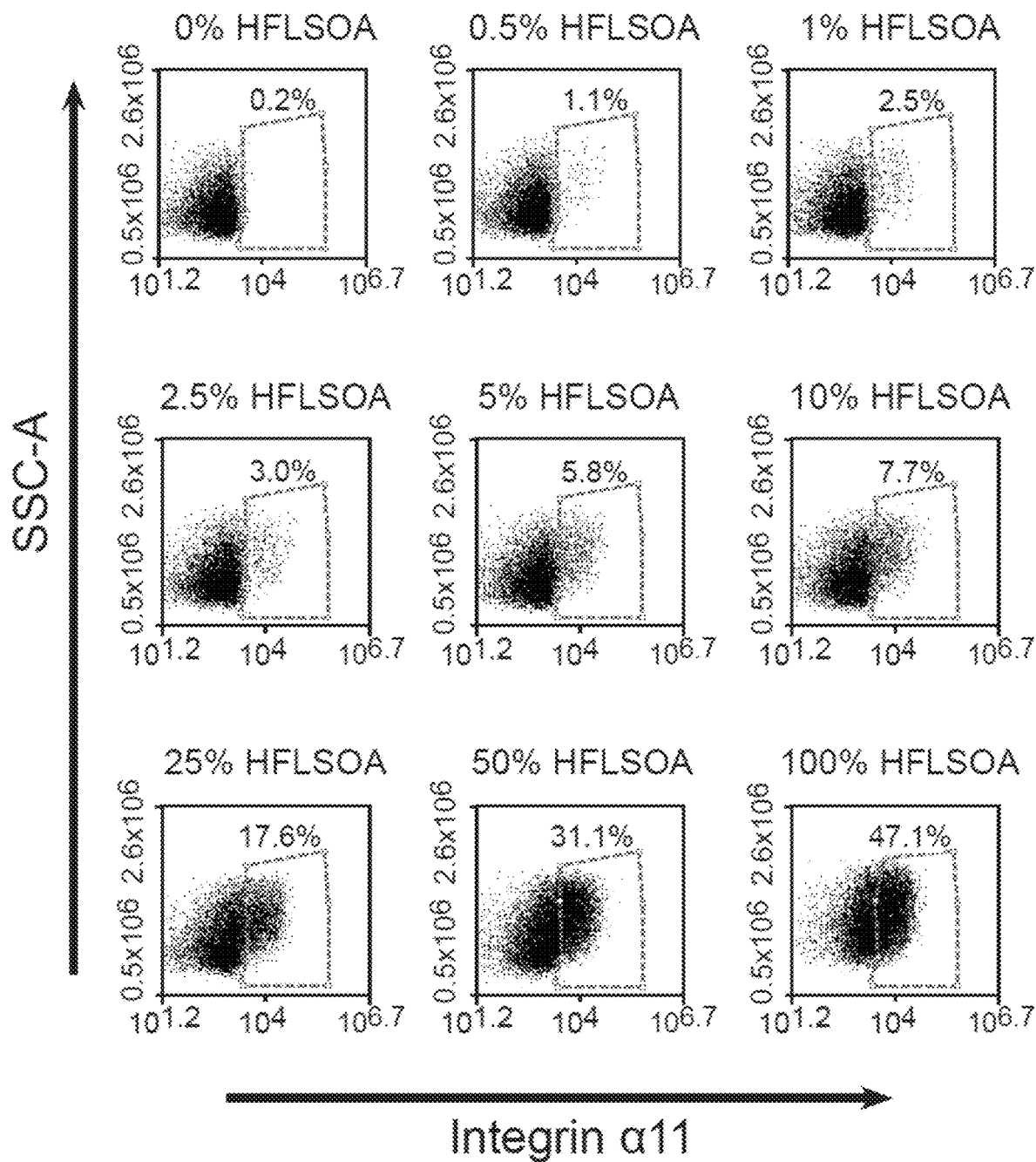
FIG. 7B. Flow cytometry analysis of integrin alpha11 beta1 on a mixture of chondrocytes and synovial fibroblast-like cells. Addition of 0, 0.5%, 1%, 2.5%, 5%, 10%, 25%, 50%, 100% HFLS-OA (human fibroblast-like chondrocytes from osteoarthritis patients) to a preparation of HNC (human nasal chondrocytes). The results show that integrin alpha11 beta1 can detect even minor amount of fibroblast-like cells in chondrocyte preparations and that integrin alpha11beta1 increases with added fibroblast-like cells.

Conclusion (I): The flow cytometry analysis demonstrated that integrin alpha11beta1 was highly expressed on HFLS and HFLS-OA, but not on chondrocytes from preparation 875 or the HNC (FIG. 7A).

Figure 7C:
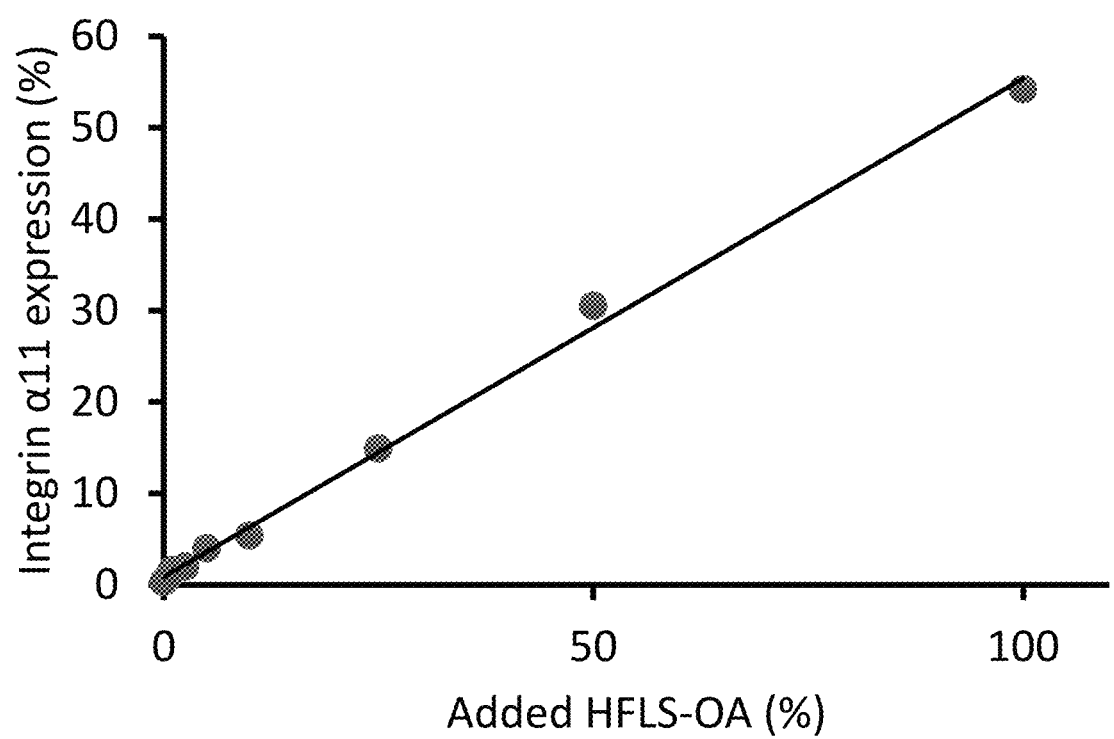
FIG. 7C. Correlation between expression of integrin alpha11beta1 and addition of HFLS-OA (human fibroblast-like chondrocytes from osteoarthritis patients) to a chondrocyte preparation. Addition of 0, 0.5%, 1%, 2.5%, 5%, 10%, 25%, 50%, and 100% of HFLS-OA to a preparation of HNC (human nasal chondrocytes). This demonstrate that integrin alpha11beta1 can be used to detect and quantify contaminating fibroblast-like cells in chondrocyte preparations.

When the sensitivity of the assay was investigated by increasing the amounts of synoviocytes (HFLS-OA) in preparations of HNC cells (FIGS. 7B and 7C), the analysis captured most of the added HFLS-OA, and was able to detect even the lowest content (0.5%) of HFLS-OA cells (FIG. 7C). The results were similar using HFLS (data not shown). Thus, analyzing integrin alpha11beta1 by flow cytometry serves as an effective method for detecting potentially contaminating fibroblasts, fibroblast-like cells or other integrin alpha11beta1-expressing cells in chondrocyte preparations and provides a sensitive way to analyze purity and quality of chondrocyte preparations.

Figure 9:
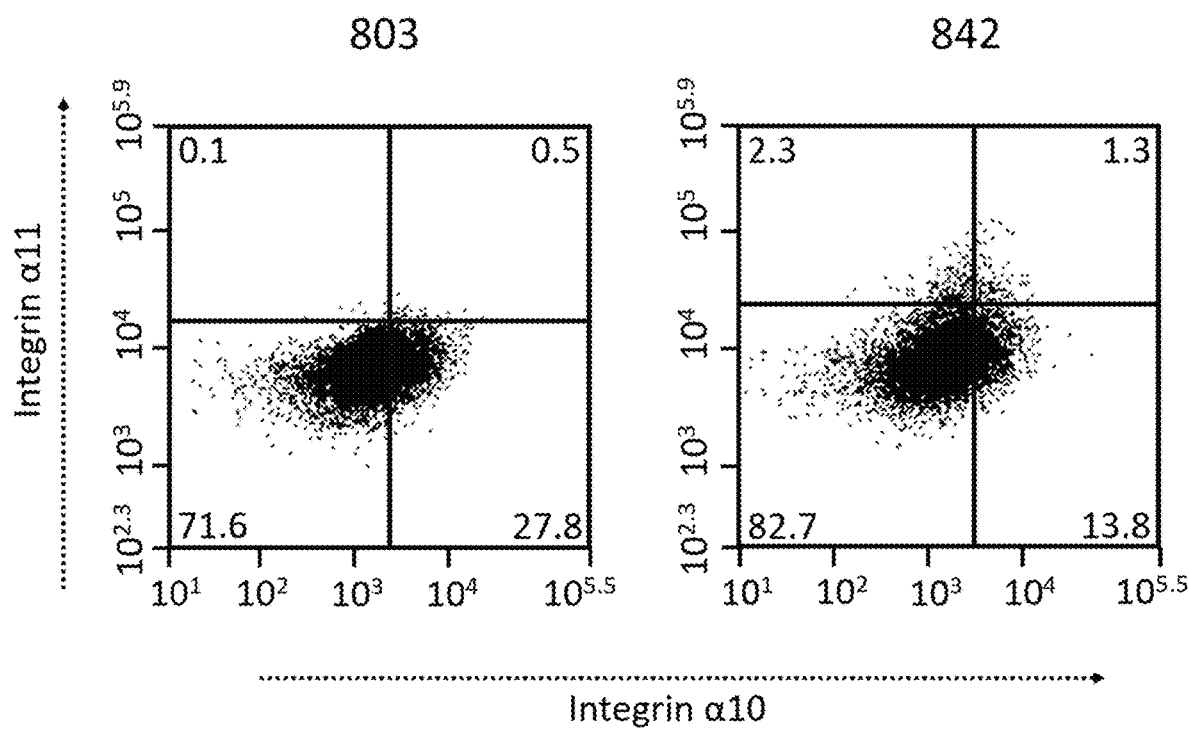
FIG. 9. Flow cytometry analysis of integrin alpha 10 (X-axis) integrin alpha 11 (Y-axis) on human chondrocyte preparation 803 (high potency see FIG. 8) and 842 (low potency). Binding of two antibodies in combination, directed to the integrins alpha10 and alpha11, respectively, was used to demonstrate the degree of single staining and double staining of the antibodies. The lower right square indicate high single expression of integrin alpha10, the upper left indicate high single expression of integrin alpha11 and the upper right indicate cells with expression of both integrins alpha10 and alpha11. The results show that the chondrocyte preparation 842 has more dedifferentated and non-chondrocytic cells compared to 803.

In addition, as shown in FIG. 9, flow cytometry analysis of integrin alpha 10 (X-axis) integrin alpha 11 (Y-axis) on human chondrocyte preparation 803 (high potency see FIG. 8) and 842 (low potency, data not shown) was conducted. Binding of two antibodies in combination, directed to the integrins alpha10 and alpha11, respectively, was used to demonstrate the degree of single staining and double staining of the antibodies.

Conclusion (II): The Flow Cytometry Analysis Demonstrate that 803 has Mainly Single expression of integrin alpha10 indicating a pure population and a high differentiated state of the chondrocytes. 842 have more integrin alpha11 expression indicating partial dedifferentiated state (cell with both alpha11 and alpha10) and also dedifferentiated and/or contaminating cells (only alpha11). This demonstrates that antibodies to integrins alpha10 and alpha11, in combination, define an integrin alpha10 to integrin alpha11 ratio, and can determine differentiation state and purity of the chondrocytes and thus the quality of the chondrocyte composition.

The invention claimed is:

1. A composition comprising isolated and cultured chondrocytes, wherein said composition has an integrin alpha10 to integrin alpha11 expression ratio of at least 4 to 1.

2. The composition according to claim 1, wherein the integrin alpha10 to integrin alpha11 expression ratio is at least 4 to 1, at least 5 to 1, at least 10 to 1, at least 15 to 1, at least 20 to 1, at least 25 to 1, at least 30 to 1, at least 35 to 1, at least 40 to 1, at least 45 to 1, at least 50 to 1, at least 60 to 1, at least 70 to 1, at least 80 to 1, at least 90 to 1, at least 100 to 1, at least 150 to 1, or at least 200 to 1.

3. The composition according to claim 1, wherein the integrin alpha11 expression is at most 25% of the integrin alpha10 expression, at most 20% of the integrin alpha10 expression, at most 15% of the integrin alpha10 expression, at most 10% of the integrin alpha10 expression, at most 5% of the integrin alpha10 expression, at most 4% of the integrin alpha10 expression, at most 3% of the integrin alpha10 expression, at most 2% of the integrin alpha10 expression, or at most 1% of the integrin alpha10 expression.

4. The composition according to claim 1, wherein the integrin alpha10 and/or integrin alpha11 is expressed as a heterodimer in combination with an integrin beta1 subunit.

5. The composition according to claim 1, wherein the composition comprises differentiated chondrocytes, and wherein said differentiated chondrocytes express integrin alpha10 and substantially no integrin alpha11.

6. The composition according to claim 1, wherein the composition comprises partially dedifferentiated chondrocytes, and wherein said partially dedifferentiated chondrocytes express both integrin alpha10 and integrin alpha11.

7. The composition according to claim 1, wherein said composition is a cartilage tissue preparation, a tissue preparation comprising chondrocytes, a monolayer chondrocyte cell culture, or a three-dimensional chondrocyte cell culture, wherein the three-dimensional chondrocyte cell culture is a spheroid, a pellet, a cell sheet or chondrocytes cultured in scaffolds.

8. The composition according to claim 1, wherein said composition is derived from a cartilage tissue, a chondrocyte comprising tissue, a monolayer chondrocyte cell culture, and a three-dimensional chondrocyte cell culture, wherein the three-dimensional chondrocyte cell culture is a spheroid, a pellet, a cell sheet or chondrocytes cultured in scaffolds.

9. The composition according to claim 1, wherein the cells in the composition are mammalian cells.

10. The composition according to claim 1, wherein the integrin alpha10 and/or the integrin alpha11 is expressed on the cell surface of a mammalian chondrocyte or a fibroblast-like cell.

11. The composition according to claim 1, wherein said composition is substantially free from contaminating cells, wherein the contaminating cells express integrin alpha11 but not integrin alpha10.

12. The composition according to claim 1, wherein said composition comprises at least 80%, at least 85%, at least 90%, at least 95%, at least 98%, at least 99%, or 100% chondrocytes, out of the total composition or population of cells.

13. The composition according to claim 1, wherein the chondrocytes further express a secondary marker selected from CEP-68/CRTAC1, GP-39 cartilage glycoprotein, CD44, CD166, Collagen IIA, Collagen IIB, Aggrecan, Alizarian Red (neg), Alcian Blue, CRTAC1, CEP-68, CD146, CD90, CD49e, CD63 and Sca-1.

14. The composition according to claim 1, wherein the chondrocytes proliferate in vitro.

15. The composition according to claim 1, wherein the chondrocytes proliferate in a monolayer culture.

* * * * *